(12) United States Patent
Thibeault et al.

(10) Patent No.: US 10,035,754 B2
(45) Date of Patent: Jul. 31, 2018

(54) CARDANOL GLYCIDYL ETHER DERIVATIVES

(71) Applicants: CENTRE DE TECHNOLOGIE MINÉRALE ET DE PLASTURGIE INC., Thetford Mines (CA); OLEOTEK INC., Thetford Mines (CA)

(72) Inventors: Dominic Thibeault, Thetford Mines (CA); François Rouillard, Victoriaville (CA); Steve Carrier, St-Jean de Brébeuf (CA); Pascal Vuillaume, Inverness (CA)

(73) Assignee: CENTRE DE TECHNOLOGIE MINÉRALE ET DE PLASTURGIE INC., Thetford Mines (CA)

( * ) Notice: Subject to any disclaimer, the term of this patent is extended or adjusted under 35 U.S.C. 154(b) by 10 days.

(21) Appl. No.: 15/309,070

(22) PCT Filed: May 1, 2015

(86) PCT No.: PCT/CA2015/000293
§ 371 (c)(1),
(2) Date: Nov. 4, 2016

(87) PCT Pub. No.: WO2015/168771
PCT Pub. Date: Nov. 12, 2015

(65) Prior Publication Data
US 2017/0073301 A1    Mar. 16, 2017

Related U.S. Application Data

(60) Provisional application No. 61/988,534, filed on May 5, 2014, provisional application No. 62/007,675, filed on Jun. 4, 2014.

(51) Int. Cl.
| | |
|---|---|
| C07C 69/533 | (2006.01) |
| C07C 43/205 | (2006.01) |
| C07C 37/00 | (2006.01) |
| C07D 303/23 | (2006.01) |
| C07C 43/20 | (2006.01) |
| C07C 69/60 | (2006.01) |
| C07C 67/16 | (2006.01) |
| C07C 69/54 | (2006.01) |
| C07D 303/28 | (2006.01) |
| C07C 67/26 | (2006.01) |
| C07C 69/593 | (2006.01) |
| C07D 203/10 | (2006.01) |
| C08F 220/32 | (2006.01) |
| C08F 122/20 | (2006.01) |
| C08F 222/20 | (2006.01) |
| C08F 22/20 | (2006.01) |

(52) U.S. Cl.
CPC .......... *C07C 69/533* (2013.01); *C07C 37/001* (2013.01); *C07C 37/002* (2013.01); *C07C 43/20* (2013.01); *C07C 43/205* (2013.01); *C07C 43/2055* (2013.01); *C07C 67/16* (2013.01); *C07C 67/26* (2013.01); *C07C 69/54* (2013.01); *C07C 69/593* (2013.01); *C07C 69/60* (2013.01); *C07D 203/10* (2013.01); *C07D 303/23* (2013.01); *C07D 303/28* (2013.01); *C08F 220/32* (2013.01); *C08F 222/20* (2013.01); *C08F 22/20* (2013.01); *C08F 122/20* (2013.01); *C08F 2220/325* (2013.01); *C08F 2222/205* (2013.01); *C08F 2500/17* (2013.01)

(58) Field of Classification Search
CPC ..... C07C 69/533; C07C 69/54; C07C 69/593; C07C 69/60; C07C 43/20; C07C 43/205; C07C 43/2055; C07C 67/26; C07C 37/001; C07C 37/002; C07C 69/002; C07D 303/23; C07D 303/28; C08F 222/20; C08F 122/20; C08F 22/20; C08F 2222/205
See application file for complete search history.

(56) References Cited

U.S. PATENT DOCUMENTS 5,683,627 A    11/1997    Katayama et al.

FOREIGN PATENT DOCUMENTS

| GB | 1279258 | 6/1972 |
| KR | 20100133681 A | * 12/2010 |
| WO | 2007077567 | 7/2007 |

OTHER PUBLICATIONS

Kim, Dong-Gyun et al, "Photo-cross-linkable star-shaped polymers with poly(ethylene glycol) and renewable cardanol side groups synthesis, characterization and application to antifouling coatings for filtration membranes", Jul. 11, 2013, Polymer Chemistry, vol. 4 Issue 19, 5065-5073.*

(Continued)

*Primary Examiner* — Ling Choi
*Assistant Examiner* — David L Miller
(74) *Attorney, Agent, or Firm* — Bereskin & Parr LLP/S.E.N.C.R.L., s.r.l.

(57) ABSTRACT

Methacrylated cardanol glycidyl ethers, diglycidyl ethers, intermediates and derivatives thereof are described herein. Compositions and polymers made with such compounds as well as methods of preparation thereof are also described. For example, compounds of Formulas: wherein n, $R_1$, $R_2$, $R_3$, $R_4$, $R_5$, and $R_6$ can each represent various different entities are described in the present disclosure.

20 Claims, No Drawings

(56) References Cited

OTHER PUBLICATIONS

Shechter, Leon et al, "Glycidyl ether reactions with alcohols, Phenols, Carboxylic acids and Acid Anhydrides" Industrial and Engineering Chemistry Jan. 1956, vol. 48 No. 1 p. 86-93.*
Abstract of Chen et al., ACS Sustainable Chem. Eng. 2015, 3(6), 1164-1171, Apr. 16, 2015.
English Abstract of KR20100133681(A), "Cardanol Derivatives, Preparation Method Thereof and Cardanol Polymer Prepared Therefrom", published on Dec. 22, 2010.
English Translation—Machine Generated of CN103554063, "Preparation method of cardanol glycidyl ether with high epoxy value", published on Feb. 5, 2014.
English Translation—Machine Generated of CN104710388, "An epoxy phenolic glycidyl ether and its preparation method and application of the cashew nut", published on Jun. 17, 2015.
English Translation—Machine Generated of KR101028337, "Highly durable heating-type epoxy resin pavement mixture for preventing the cracking and deformation of a concrete road and a construction process thereby", published on Apr. 11, 2011.
English Translation—Machine Generated of KR20120109052, "Forming method of cardanol derivative polymer film capable of quickly forming a film and being cured by electron beams, and a coating film manufactured by the same", published on Oct. 8, 2012.
Jaillet et al., "New biobased epoxy materials from cardanol", Eur. J. Lipid Sci. Technol. 2014, 116, 63-73.
Jaillet et al., "Synthesis and characterization of novel vinylester prepolymers from cardanol", Eur. J. Lipid Sci. Technol. 2014, 116, 0000-0000.
Kim et al., "Photo-cross-linkable star-shaped polymers with poly-(ethylene glycol) and renewable cardanol side groups: synthesis, characterization, and application to antifouling coatings for filtration membranes", Polymer Chemistry 2013, 4, 5065-5073.
Patel et al., "Glass-fibre-reinforced Epoxy Composites using Epoxidized Cardanol as Diluent", High Performance Polymers 1991, 3(2), 107-111.

* cited by examiner

CARDANOL GLYCIDYL ETHER DERIVATIVES

The present application is a 35 USC 371 national stage entry of PCT/CA2015/000293 filed on May 1, 2015 and which claims priority on U.S. 61/988,534 filed on May 5, 2014, on U.S. 62/007,675 filed on Jun. 4, 2014. These documents are hereby incorporated by reference in their entirety.

The present disclosure relates to compounds (that can be used as monomers) and compositions that can comprise methacrylated cardanol glycidyl ethers, diglycidyl ethers, derivatives and/or intermediates thereof. Moreover, the present disclosure also relates to polymers obtained from such methacrylated cardanol glycidyl ethers, diglycidyl ethers, derivatives and/or intermediates thereof. The present disclosure also relates to processes for preparing such compounds, derivatives, intermediates compositions and polymers. For example, such compounds, derivatives, intermediates, compositions and polymers can be prepared by using biobased starting material. For example, such compounds, derivatives, intermediates, compositions and polymers can be biosourced.

BACKGROUND

Increasing cost of oil products and legal restriction of governments on environmental and health impacts of styrene make so that it will be more and more necessary to develop new polymeric materials safer, eco-friendly and from renewable resources.

SUMMARY

According to one aspect, there are provided methacrylated cardanol glycidyl ethers, diglycidyl ethers, derivatives, and intermediates thereof as well as compositions and polymers made with such compounds.

According to another aspect, the present disclosure relates to polymers useful in applications including Hand lay-up processes, hand spray up processes, RTM (resin transfer molding) processes, prepregs and SMC, compression molding and vacuum bagging.

In a further aspect, the present disclosure relates to a process for the production of methacrylated cardanol glycidyl ethers, diglycidyl ethers, intermediates and derivatives thereof. Methods for preparing compositions as well as polymers made with such entities are also disclosed herein.

In an embodiment, the present disclosure includes a compound of Formula:

(III)

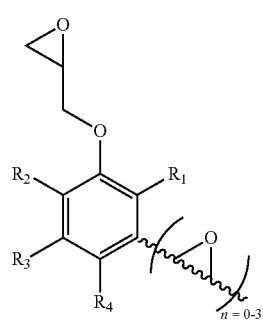

wherein:

$R_1$, $R_2$, $R_3$ and $R_4$ are independently chosen from H, F, Cl, Br, I, OH, O-alkyl, O-aryl, O-acyl and aryl; and

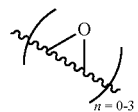

is chosen from

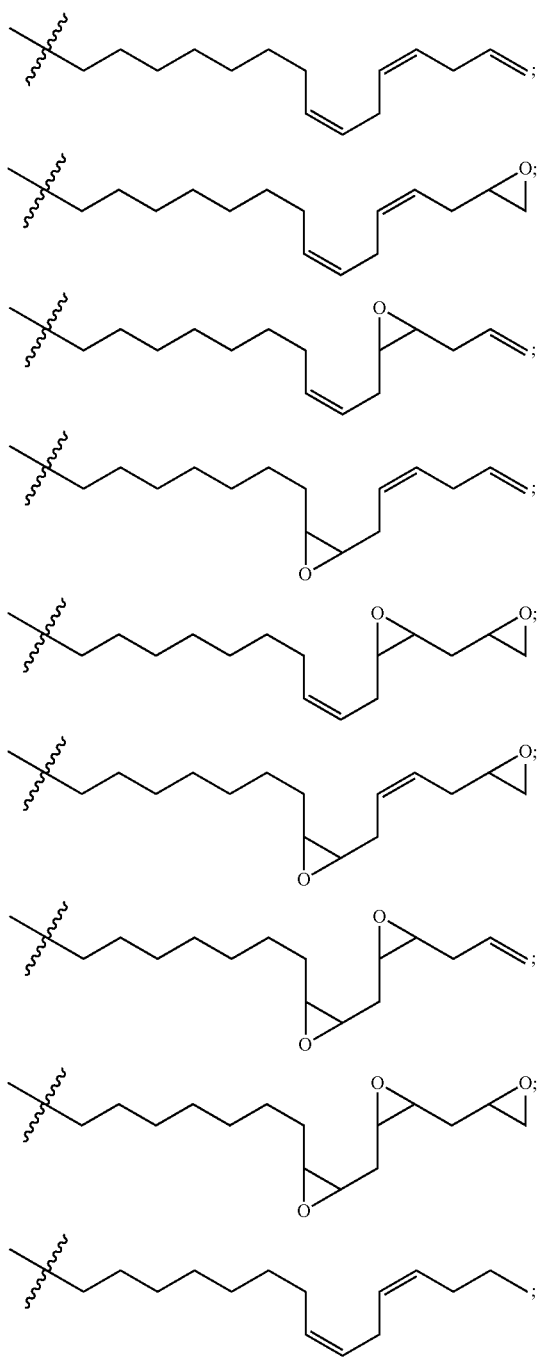

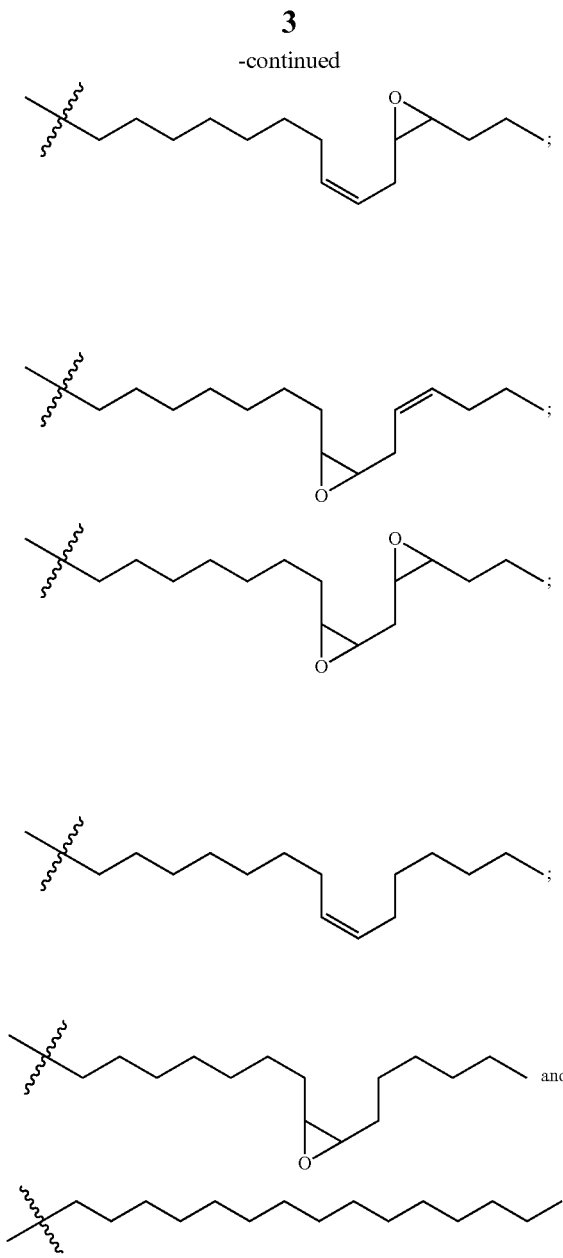
In an embodiment, the present disclosure includes a compound of Formula:
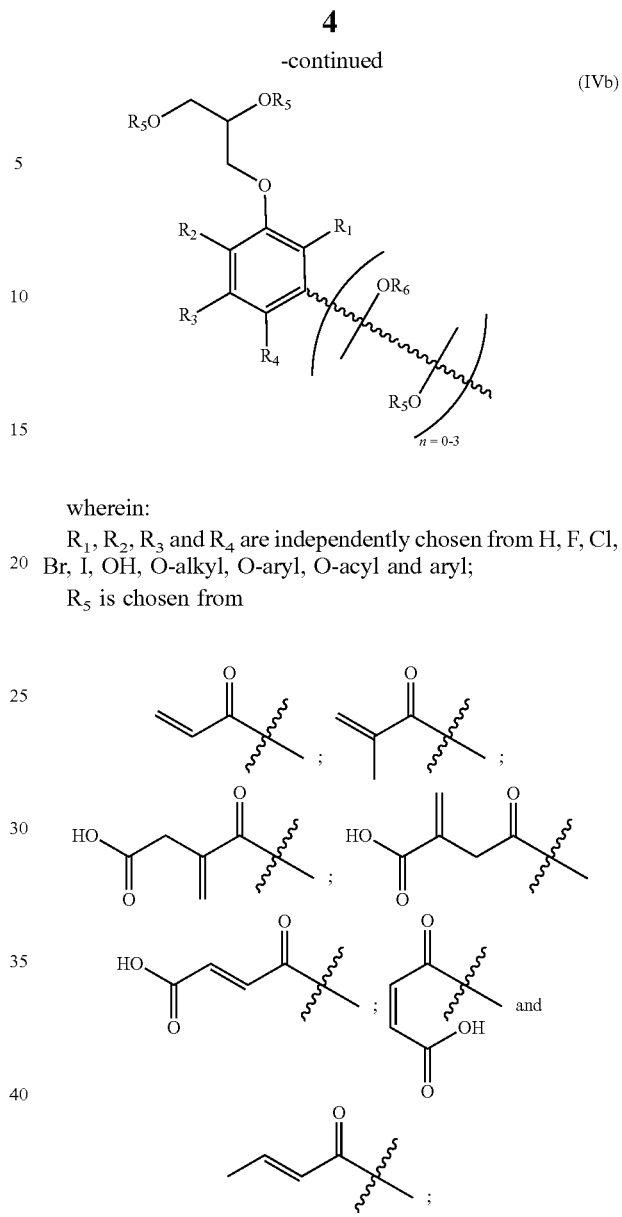
wherein:
$R_1$, $R_2$, $R_3$ and $R_4$ are independently chosen from H, F, Cl, Br, I, OH, O-alkyl, O-aryl, O-acyl and aryl;
$R_5$ is chosen from
$R_6$ is H or acyl;
is chosen from
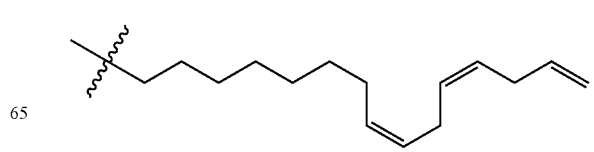

-continued
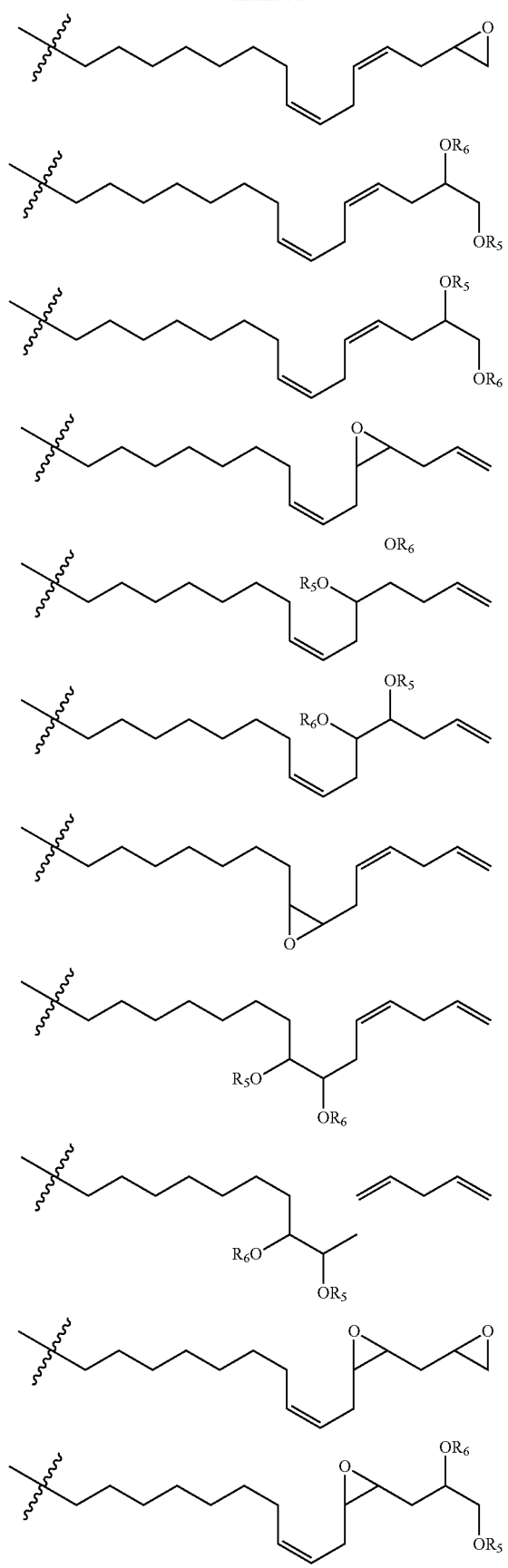
-continued
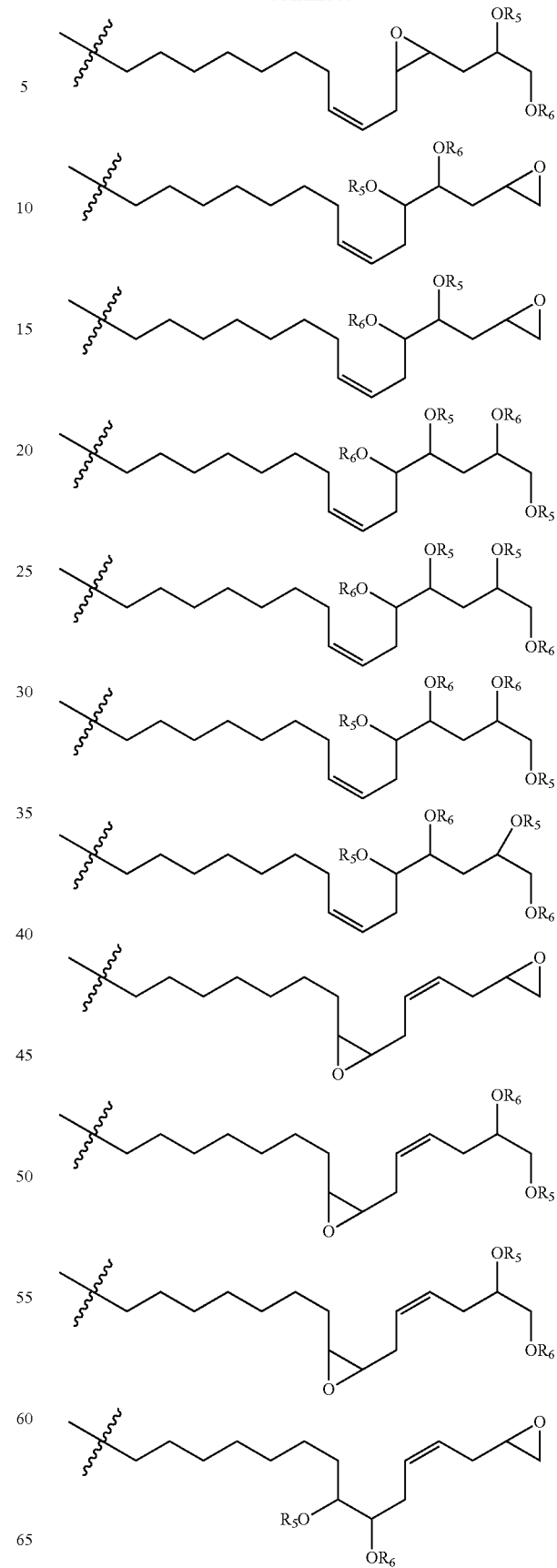

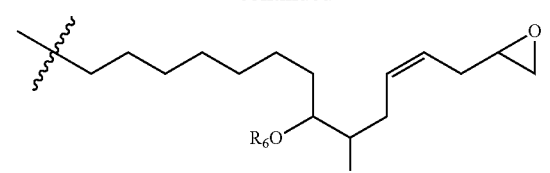
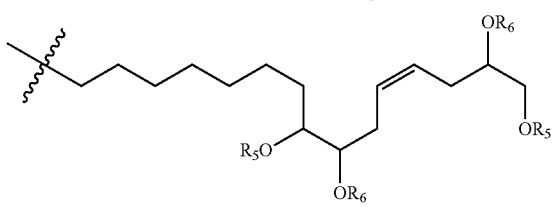
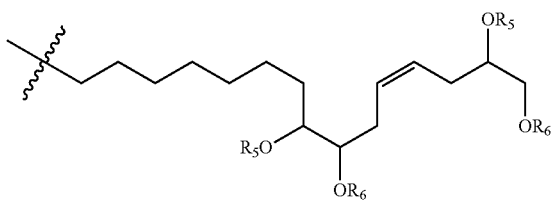
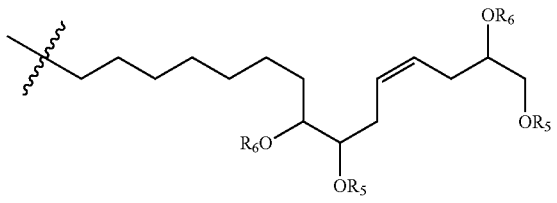
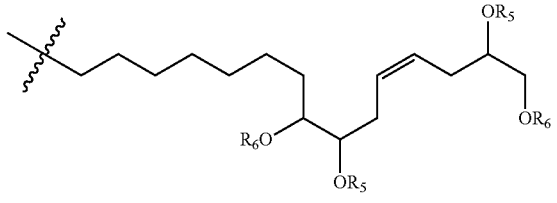
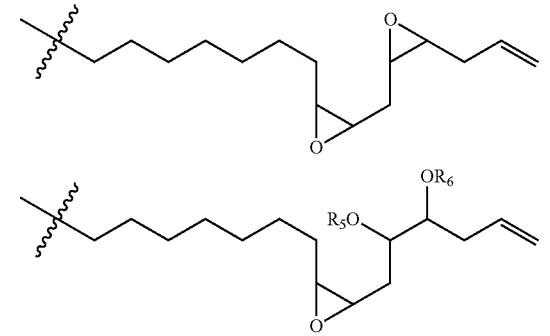
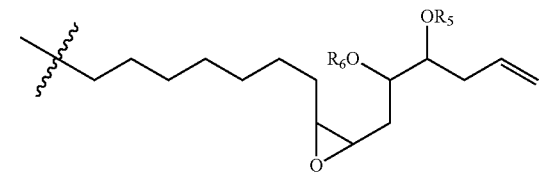
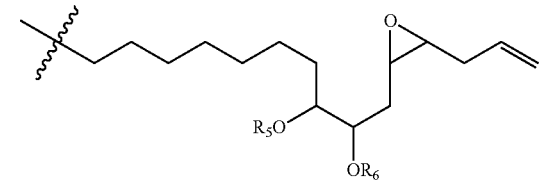
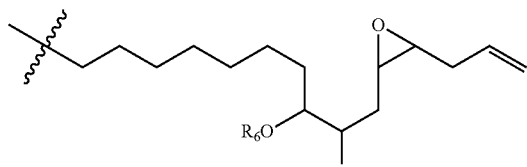
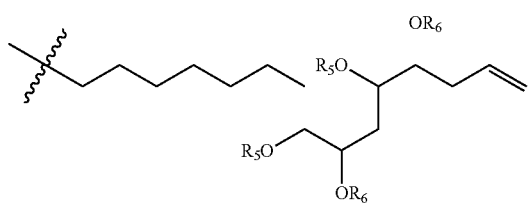
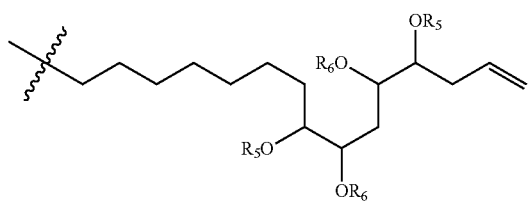
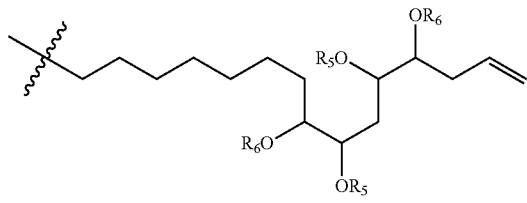
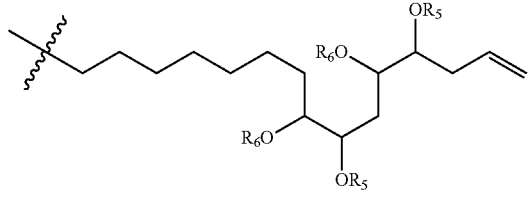
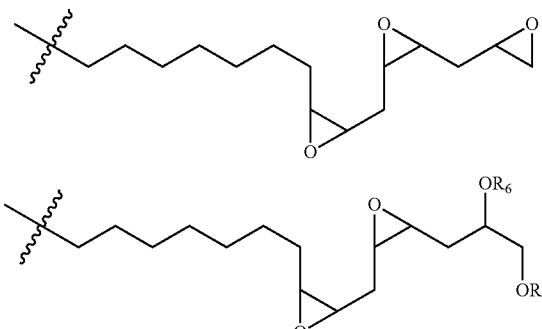
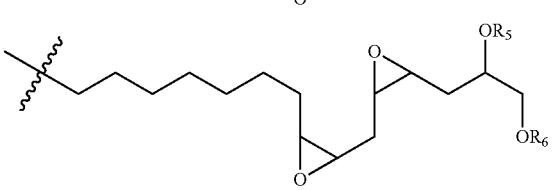
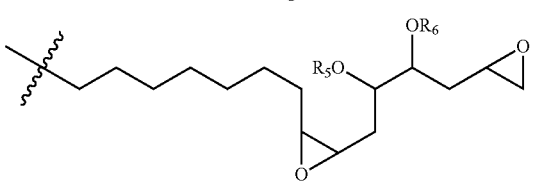

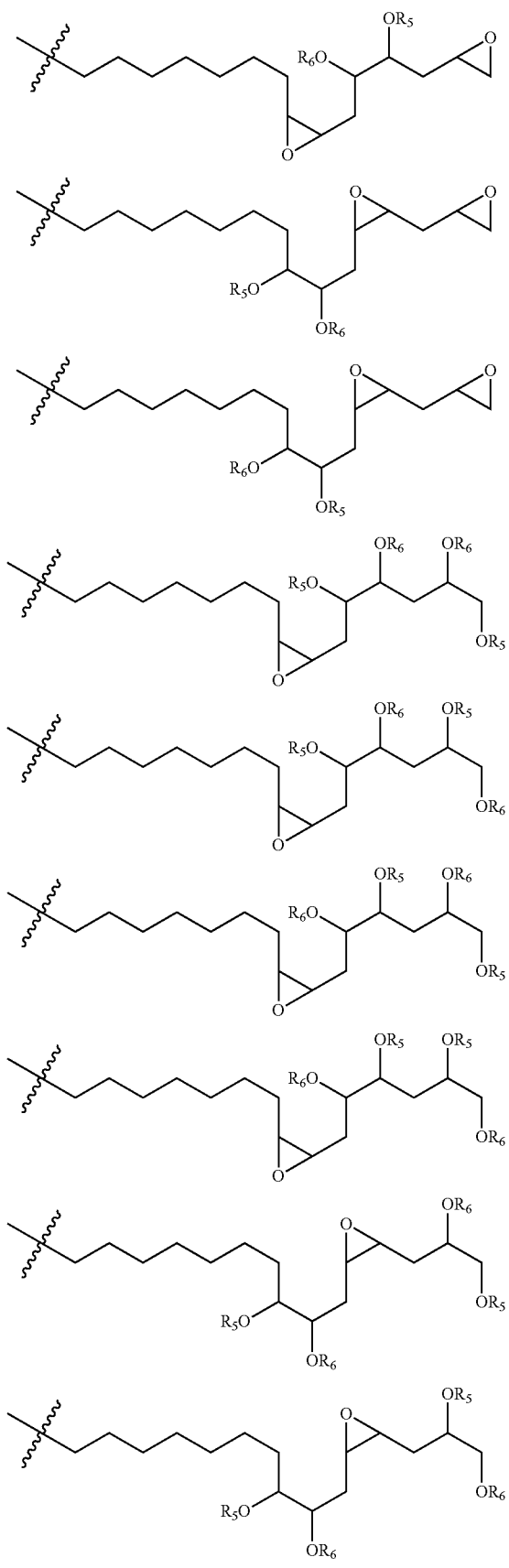
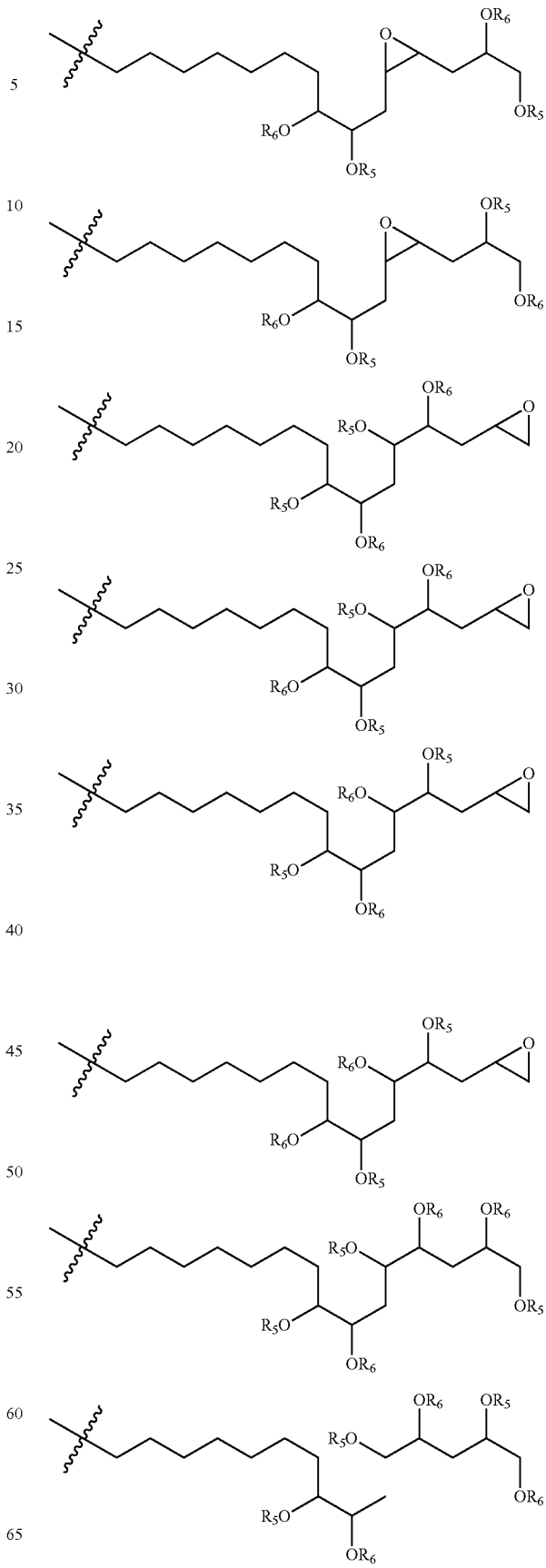

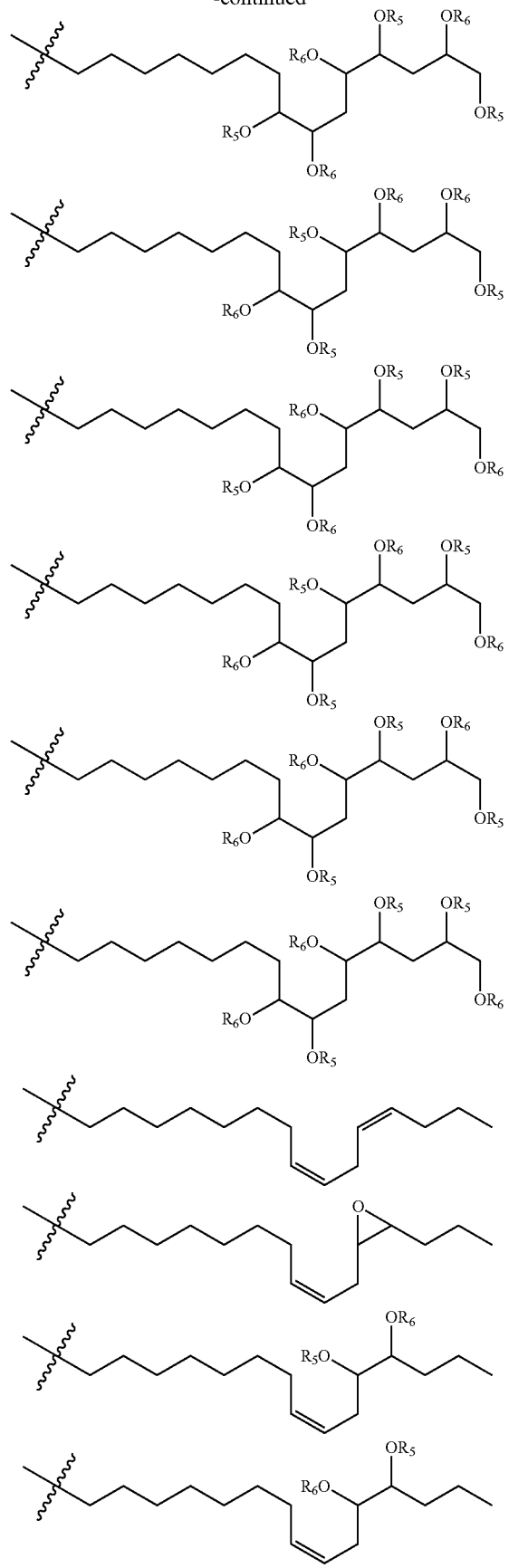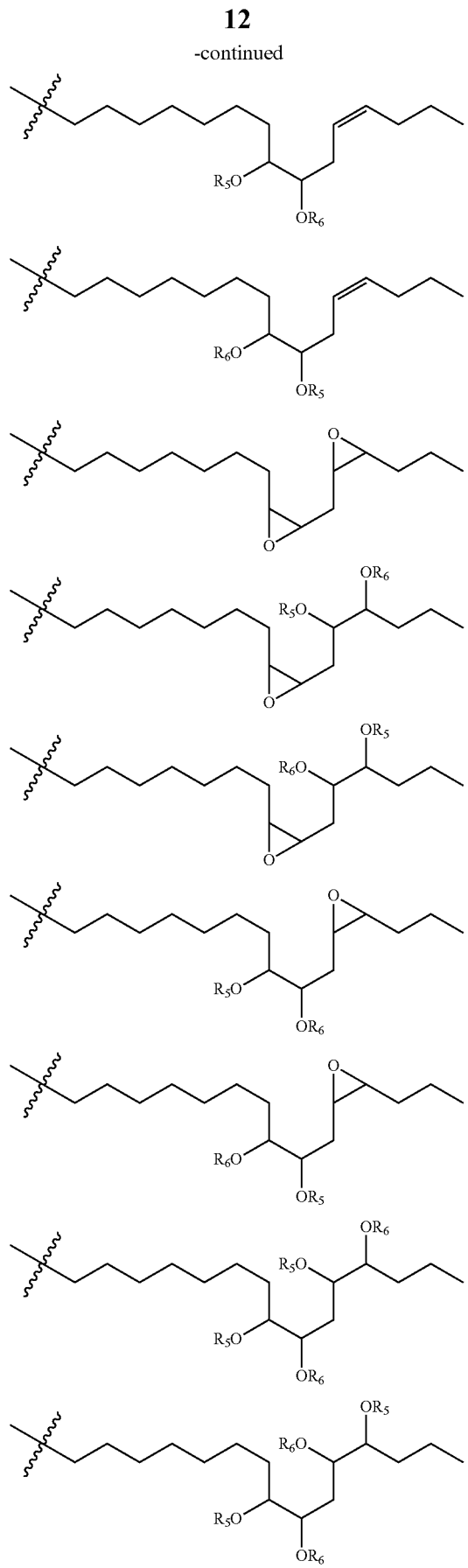

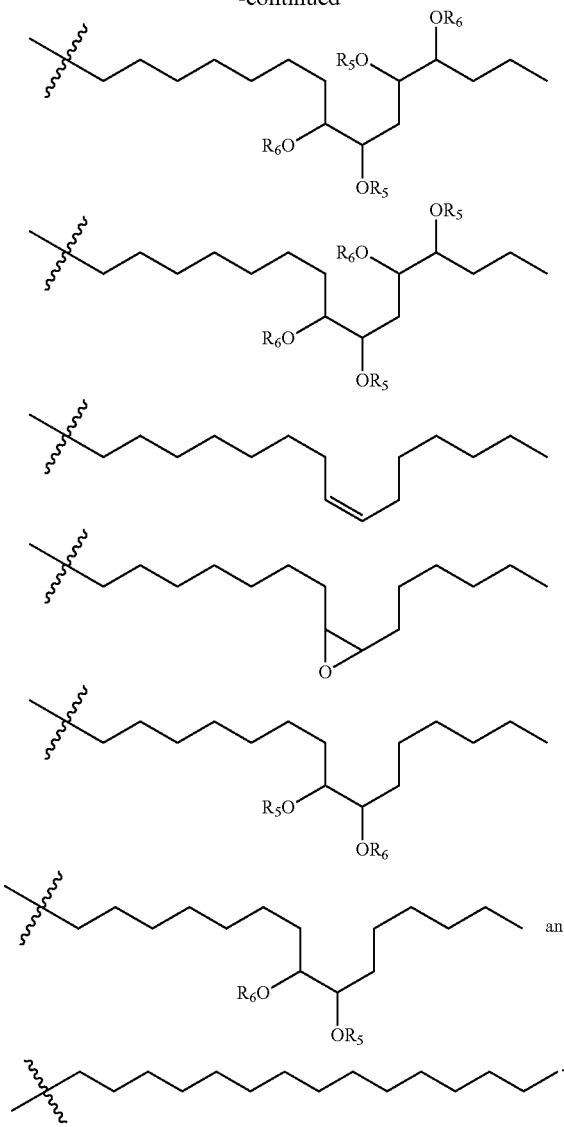
In an embodiment, the present disclosure includes a compound of Formula:
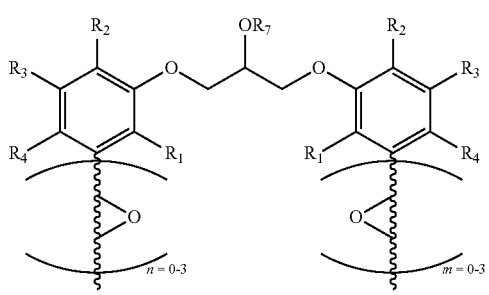
wherein:
$R_1$, $R_2$, $R_3$ and $R_4$ are independently chosen from H, F, Cl, Br, I, OH, O-alkyl, O-aryl, O-acyl and aryl;
$R_7$ is chosen from H, alkyl, aryl and acyl;
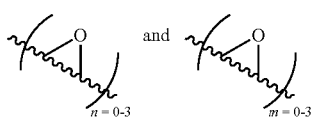
are independently chosen from
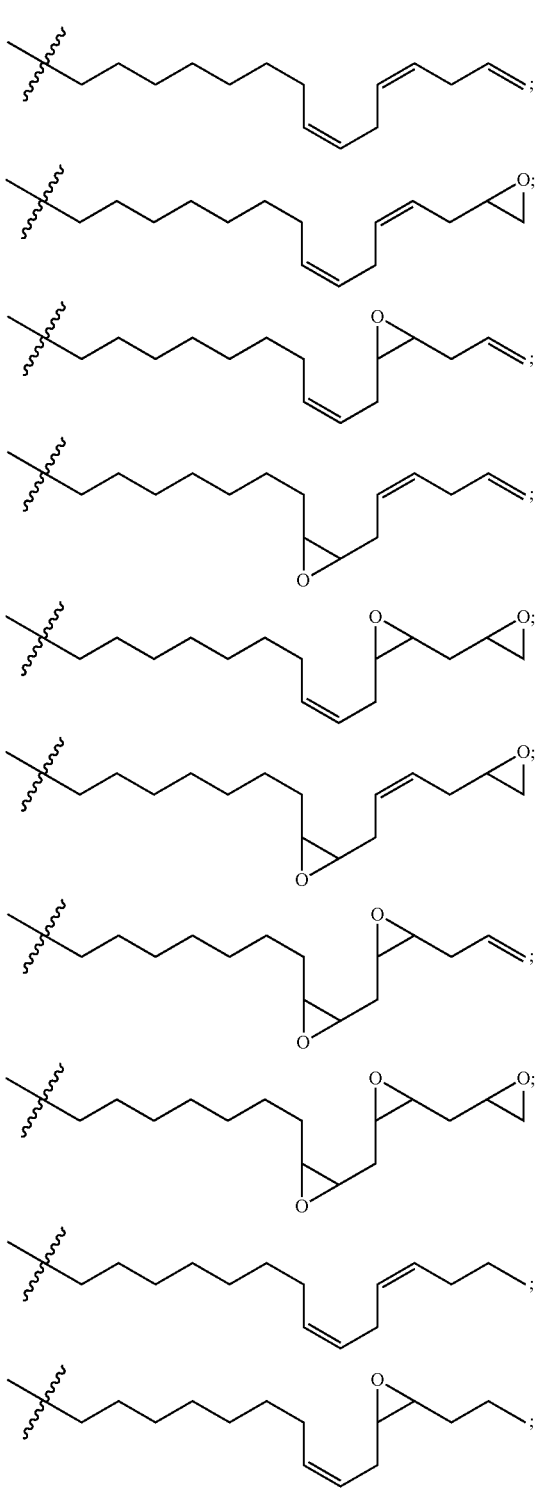

-continued
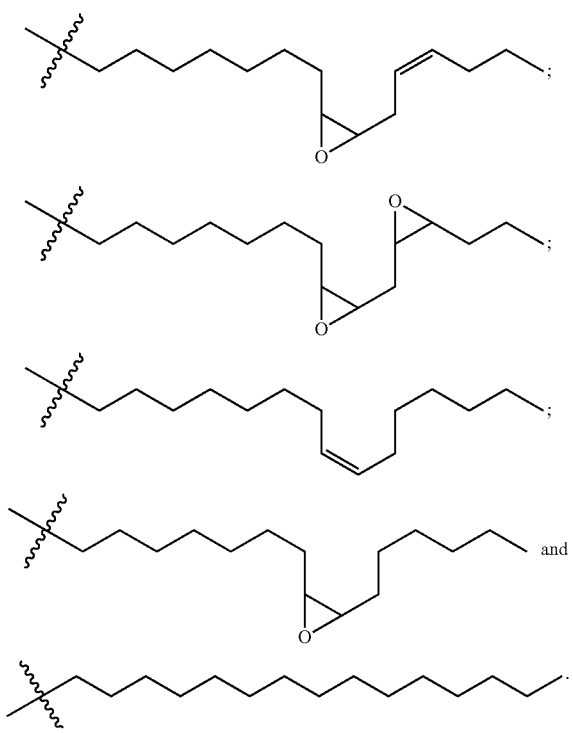
In an embodiment, the present disclosure includes a compound of Formula:
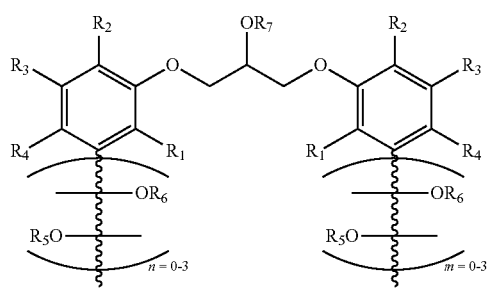
wherein:
R₁, R₂, R₃ and R₄ are independently chosen from H, F, Cl, Br, I, OH, O-alkyl, O-aryl, O-acyl and aryl;
R₇ is chosen from H, alkyl, aryl and acyl;
R₅ is chosen from
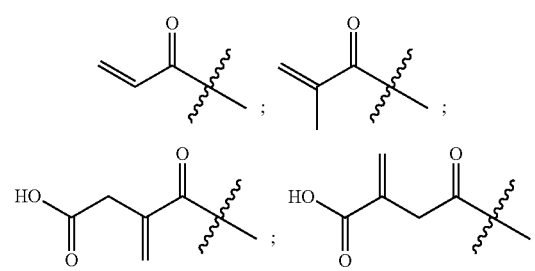
-continued
R₆ is H or acyl;
are independently chosen from 17
-continued
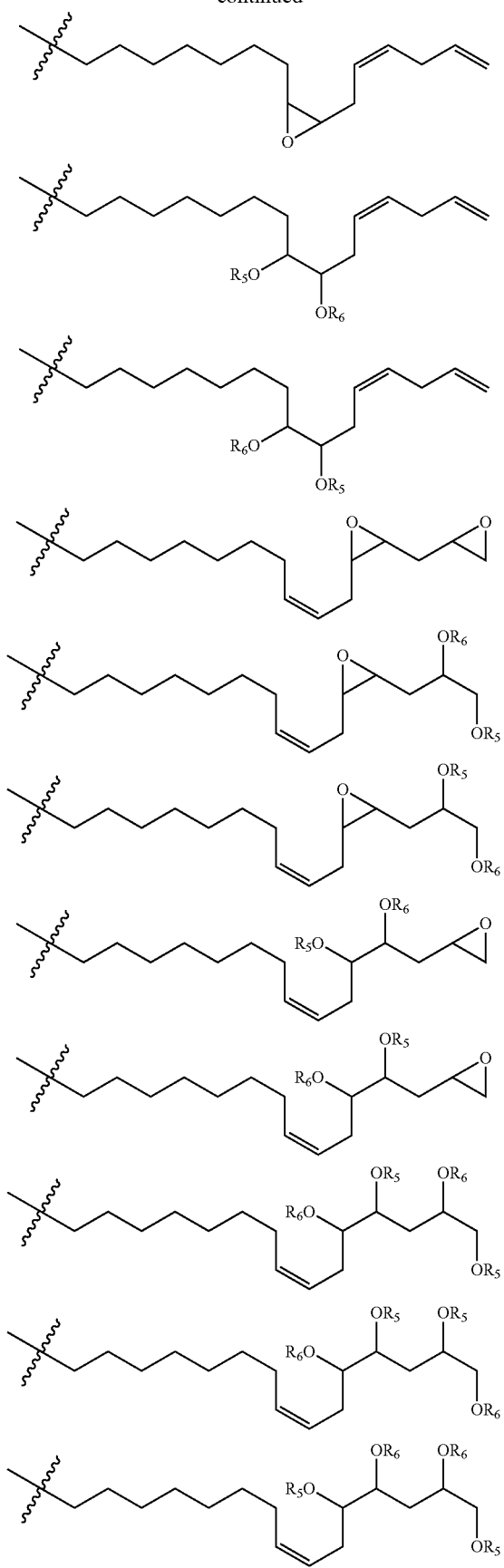
18
-continued
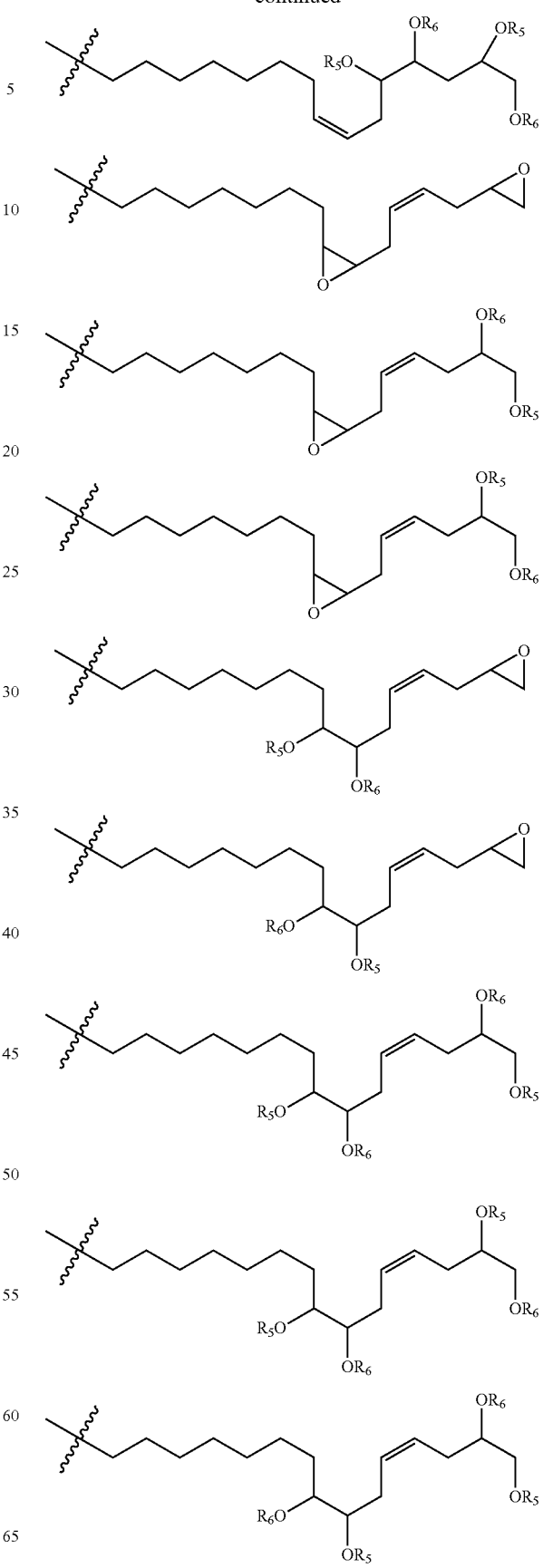

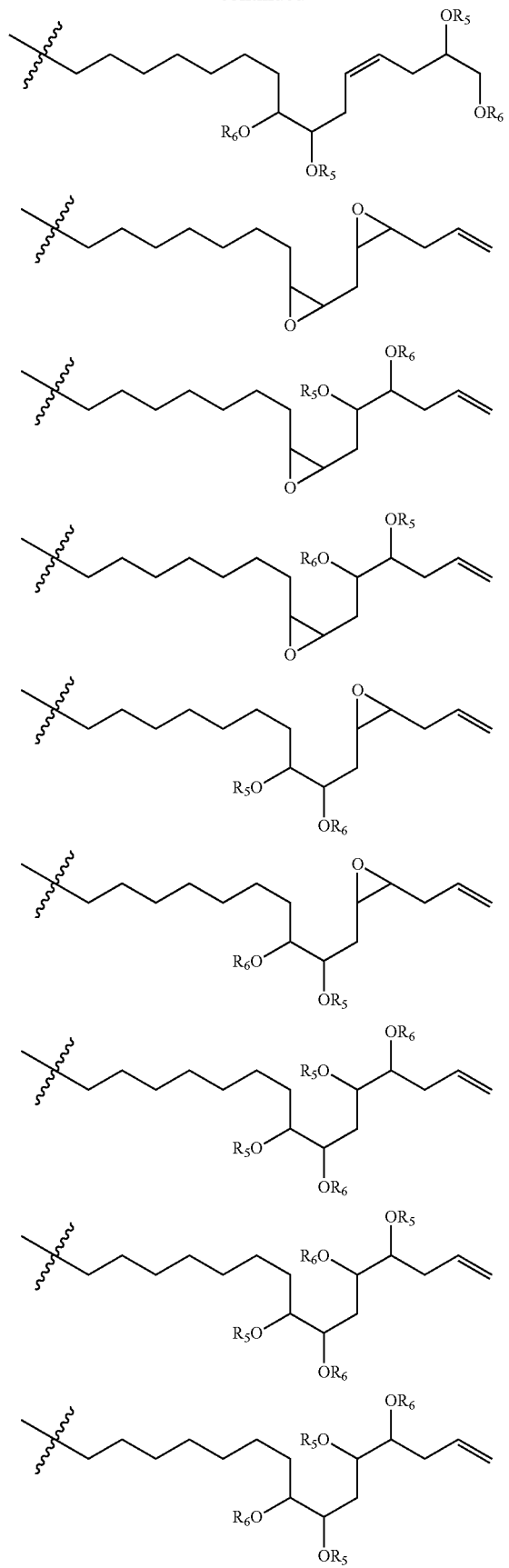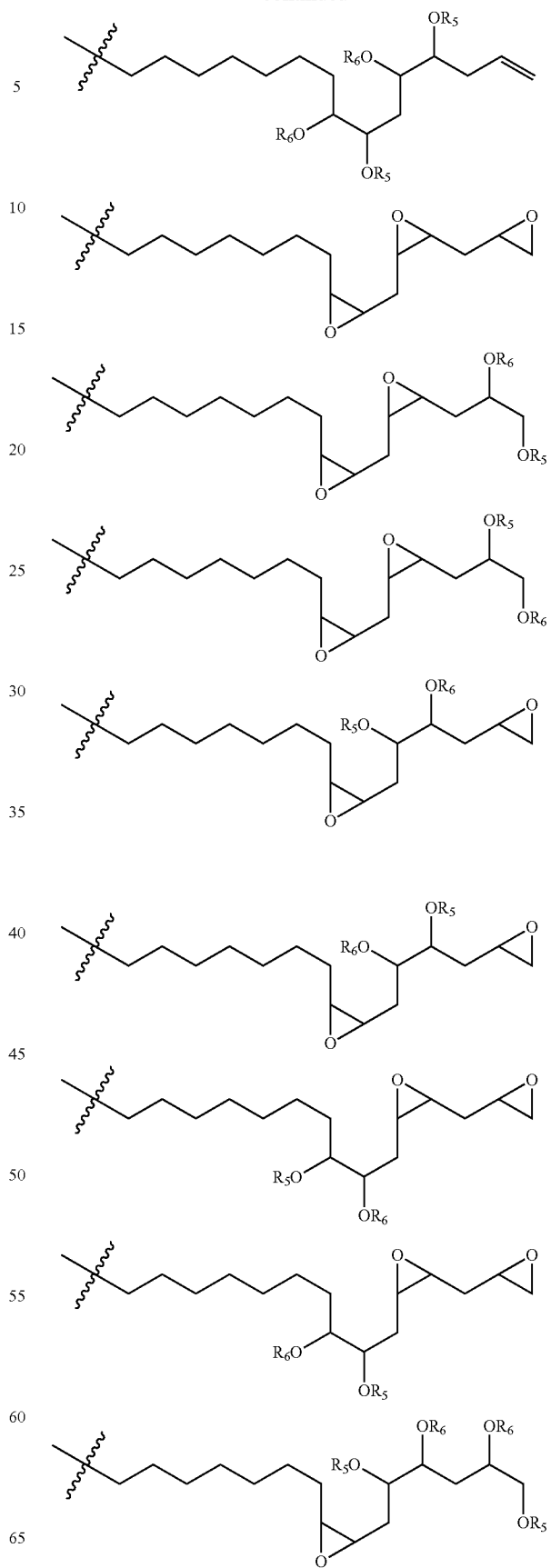

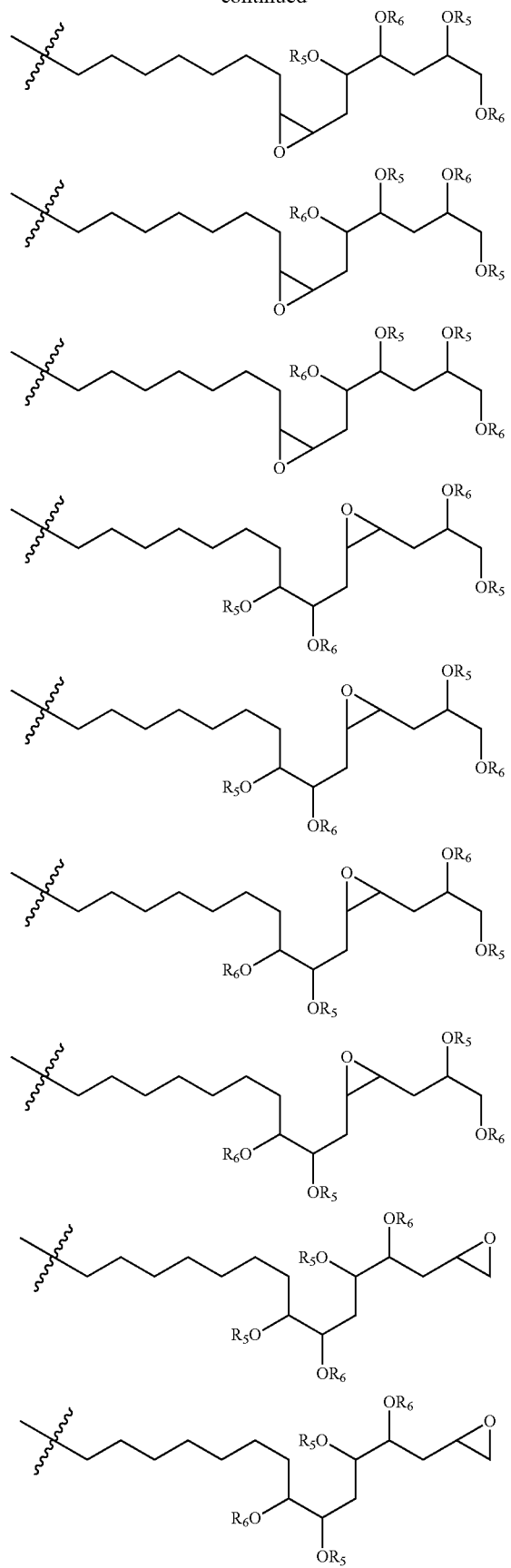
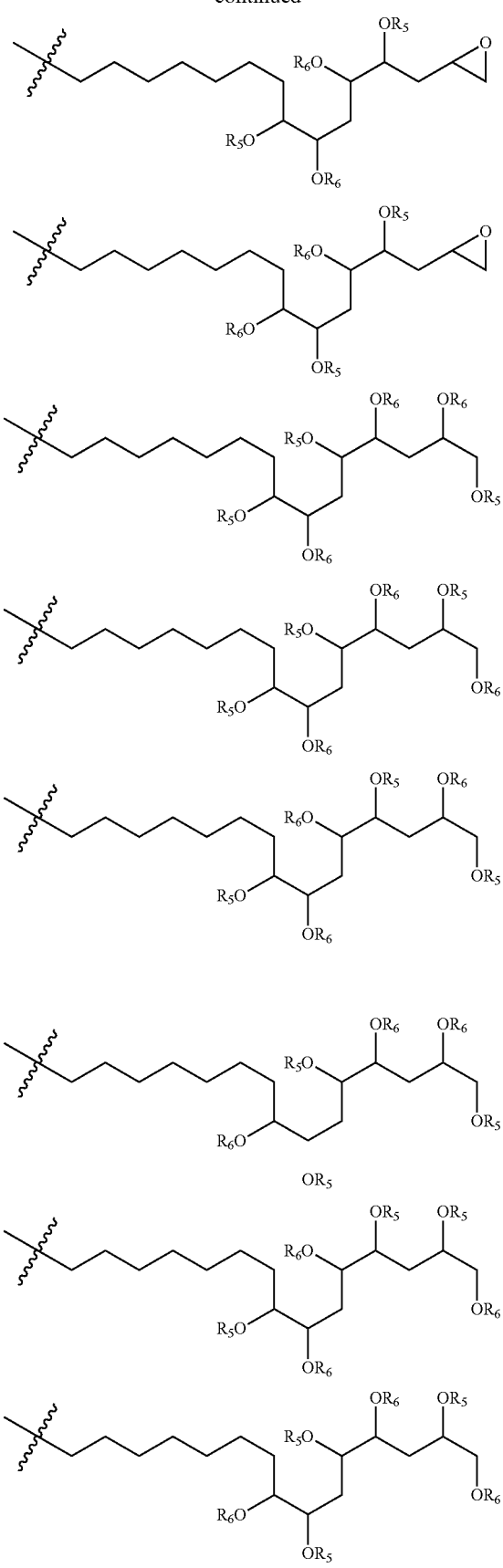

23
-continued
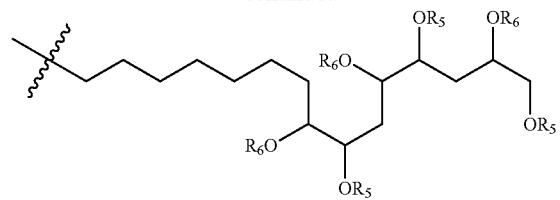
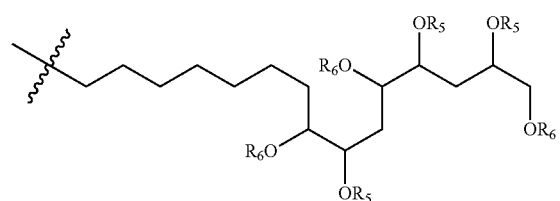
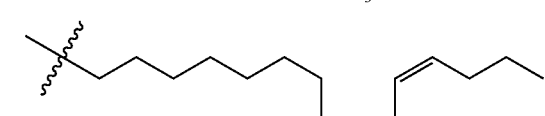
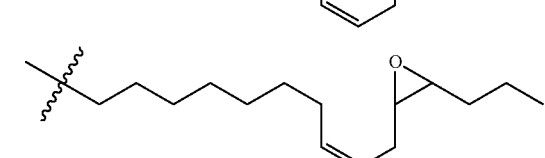
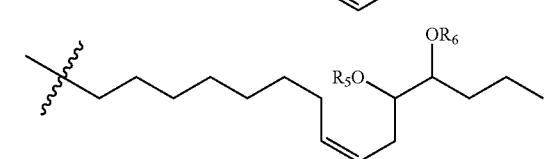
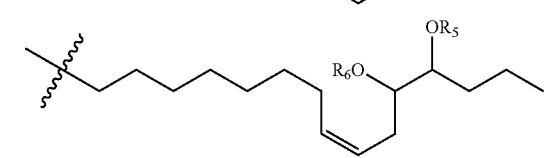
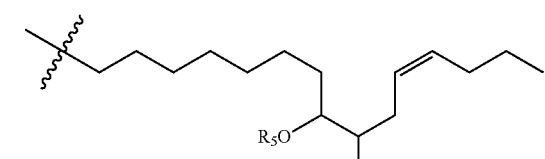
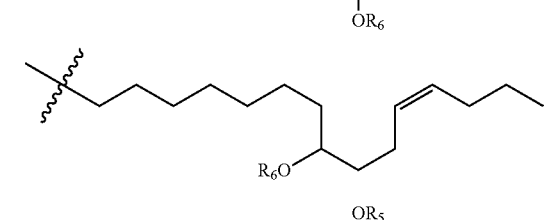
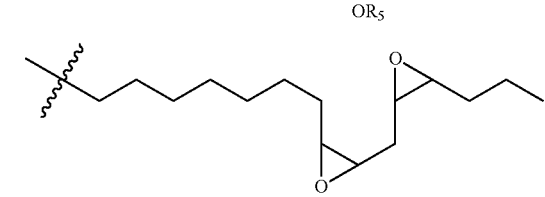
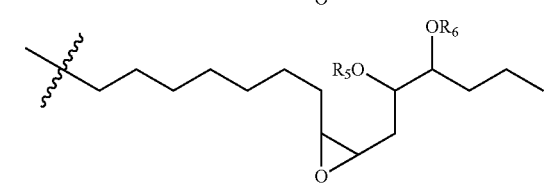
24
-continued
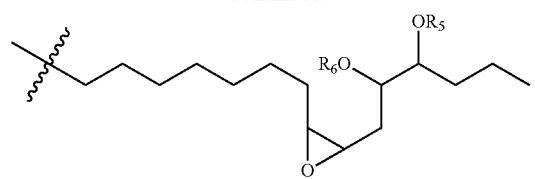
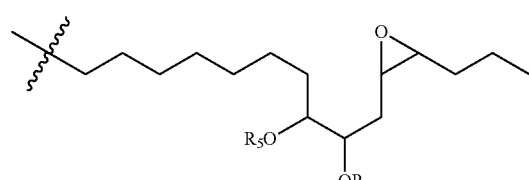
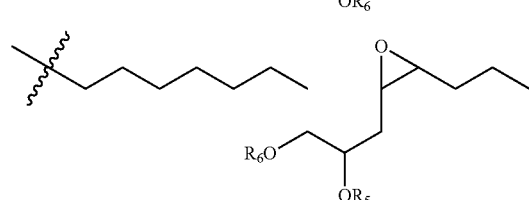
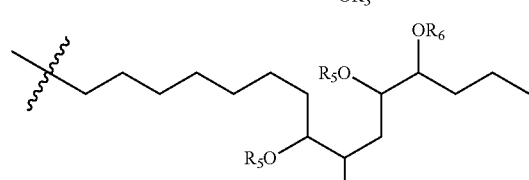
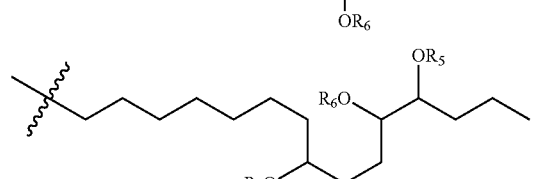
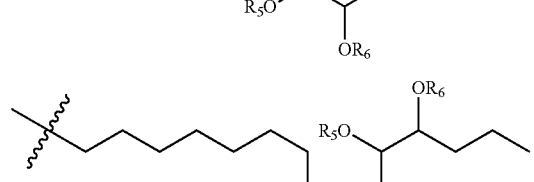
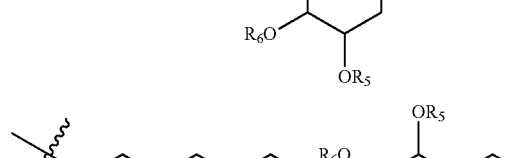
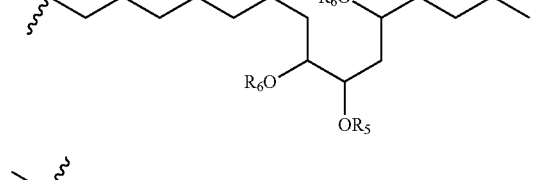
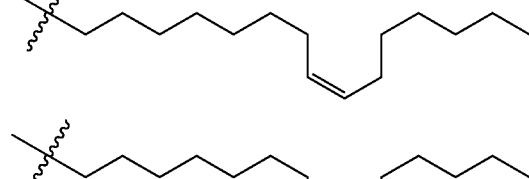
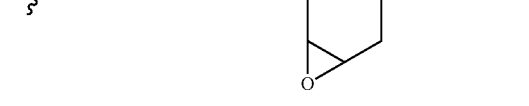

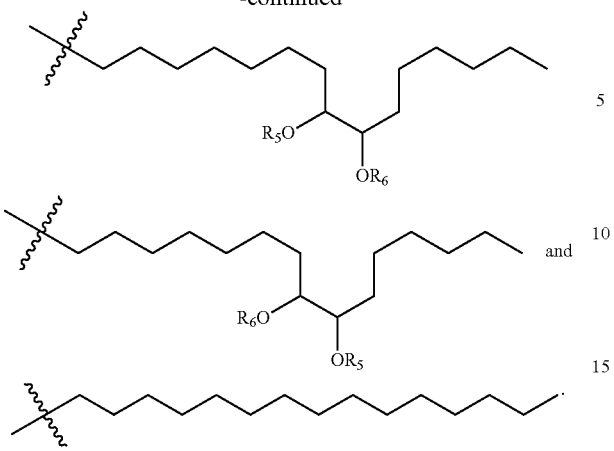

In an embodiment, $R_1$, $R_2$, $R_3$ and $R_4$ are independently chosen from H, F, Cl, Br, I, OH, O-alkyl, O-aryl, O-acyl and aryl;

In an embodiment, $R_1$, $R_2$, $R_3$ and $R_4$ is H.
In an embodiment, $R_7$ is H.
In an embodiment, $R_7$ is acetyl.
In an embodiment, $R_5$ is

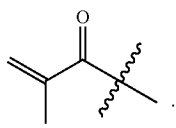 [SMILES: *C(=O)C(=C)C]

In an embodiment, $R_6$ is H.
In an embodiment, $R_6$ is acetyl.
In an embodiment, the present disclosure includes a composition comprising at least one compound as defined in the present disclosure and a reactive diluent.

In an embodiment, the present disclosure includes a composition comprising at least one compound as defined in the present disclosure and at least one additive chosen from a reactive diluent, a defoaming agent and a promoter.

In an embodiment, the present disclosure includes a composition comprising at least one compound as defined in the present disclosure and at least one additive chosen from a reactive diluent, a defoaming agent, a promoter and a photoinitiator.

In an embodiment, the reactive diluent comprises at least one compound chosen from

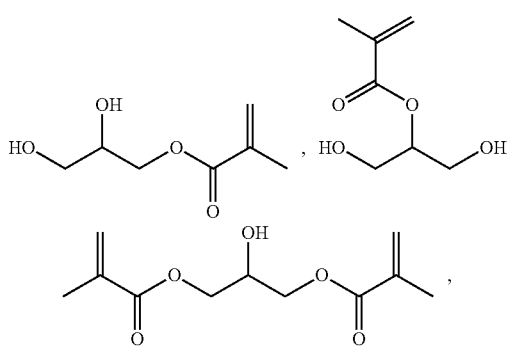

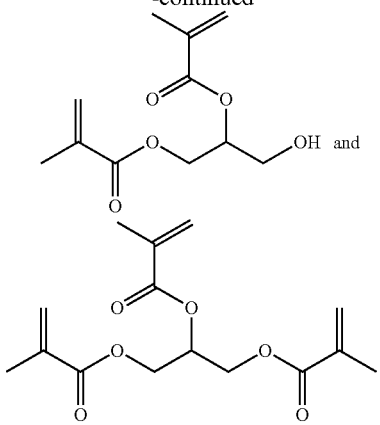

In an embodiment, said reactive diluent comprises

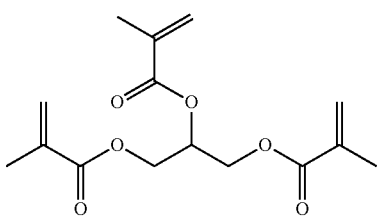

In an embodiment, the composition comprises a promoter that comprises at least one of a cobalt derivative and at least one aniline derived compound.

In an embodiment, the cobalt derivative comprises cobalt naphthenate and cobalt 2-ethylhexanoate.

In an embodiment, the aniline derived compound comprises an N,N'-dialkylaniline.

In an embodiment, the N,N'-dialkylaniline comprises dimethylaniline and diethylaniline.

In an embodiment, the composition comprises about 0.01% to about 1% (w/w) of the promoter.

In an embodiment, the composition comprises about 0.05% to about 0.5% (w/w) of the promoter.

In an embodiment, the composition comprises about 0.01% to about 2% (w/w) of the defoaming agent.

In an embodiment, the composition comprises about 0.1% to about 1% (w/w) of the defoaming agent.

In an embodiment, the composition is a thermosetting composition.

In an embodiment, the present disclosure includes polymer obtained by polymerizing a compound as defined in the present disclosure.

In an embodiment, the present disclosure includes a polymer obtained by reacting a composition as defined in the present disclosure with a polymerization catalyst.

In an embodiment, the present disclosure includes a polymer obtained by exposing a composition as defined in the present disclosure to a light suitable for initializing polymerisation In an embodiment, the present disclosure includes a method for preparing a monomer, the method comprising:
    optionally isomerizing at least one double bond of cardanol or of a derivative thereof;
    reacting the cardanol or derivative thereof with epichlorohydrin to obtain a cardanol glycidyl ether or a derivative thereof;

epoxidizing at least one double bond of the cardanol glycidyl ether or derivative thereof to obtain a side chain epoxidized derivative; and reacting said side chain epoxidized derivative with a nucleophile chosen from acrylic acid, methacrylic acid, maleic acid, fumaric acid, itaconic acid and crotonic acid.

In an embodiment, the present disclosure includes a method for preparing a monomer, the method comprising:

optionally isomerizing at least one double bond of cardanol or of a derivative thereof;

reacting the cardanol or derivative thereof with epichlorohydrin to obtain a cardanol glycidyl ether or a derivative thereof;

epoxidizing at least one double bond of the cardanol glycidyl ether or derivative thereof; and reacting the at least one epoxidized double bond and/or oxirane group of the epichlorohydrin with a nucleophile chosen from acrylic acid, methacrylic acid, maleic acid, fumaric acid, itaconic acid and crotonic acid.

In an embodiment, the present disclosure includes a method for preparing a monomer, the method comprising:

optionally isomerizing at least one double bond of cardanol or of a derivative thereof;

reacting the cardanol or derivative thereof with epichlorohydrin to obtain a cardanol glycidyl diether comprising a pair of side chains or a derivative thereof;

epoxidizing at least one double bond on the pair of side chains of the cardanol glycidyl diether to obtain a side chain epoxidized derivative;

reacting said side chain epoxidized derivative with a nucleophile chosen from acrylic acid, methacrylic acid, maleic acid, fumaric acid, itaconic acid and crotonic acid.

In an embodiment, the present disclosure includes the use of at least one compound of the present disclosure in the preparation of a polymer.

In an embodiment, the present disclosure includes the use of at least one derivative of the present disclosure in the preparation of a polymer.

In an embodiment, the present disclosure includes the use of at least one intermediate of the present disclosure in the preparation of a polymer.

In an embodiment, the present disclosure includes the use of at least one monomer of the present disclosure in the preparation of a polymer.

In an embodiment, the present disclosure includes the use of at least one composition of the present disclosure in the preparation of a polymer.

In an embodiment, the present disclosure includes a method for preparing a polymer, the method comprises polymerizing at least one compound as described in the present disclosure.

In an embodiment, the present disclosure includes a method for preparing a polymer, the method comprises polymerizing at least one derivative as described in the present disclosure.

In an embodiment, the present disclosure includes a method for preparing a polymer, the method comprises polymerizing at least one intermediate as described in the present disclosure.

In an embodiment, the present disclosure includes a method for preparing a polymer, the method comprises polymerizing at least one composition as described in the present disclosure.

In an embodiment, the present disclosure includes a polymer obtained by exposing a composition as defined in the present disclosure to a light suitable for initializing polymerisation.

In an embodiment, the present disclosure includes a polymer obtained by reacting a composition as defined in the present disclosure with a polymerization catalyst.

For example, polymerization can be carried out by reacting the monomer, derivative, compound, intermediate or composition with a catalyzer, a light, heat and combinations thereof.

For example, n can be an integer that is 0, 1, 2 or 3.

For example, n can be an integer that is 0, 1, 2 or 3.

For example, the composition can be a thermosetting composition (thermosetting resin or thermoset).

The foregoing and other advantages and features of the present disclosure will become more apparent upon reading of the following non-restrictive description of illustrative embodiments thereof, given by way of example only.

DETAILED DESCRIPTION

I. Glossary

In order to provide a clear and consistent understanding of the terms used in the present disclosure, a number of definitions are provided below. Moreover, unless defined otherwise, all technical and scientific terms as used herein have the same meaning as commonly understood by one of ordinary skill in the art to which this specification pertains.

The word "a" or "an" when used in conjunction with the term "comprising" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The expression "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of ±10% of the modified term if this deviation would not negate the meaning of the word it modifies.

As used herein, the term "alkyl" includes both straight-chain and branched. This also applies if they carry substituents or occur as substituents on other residues, for example in alkoxy residues, alkoxycarbonyl residues or arylalkyl residues. Substituted alkyl residues are substituted in any suitable position. Examples of alkyl residues containing from 1 to 10 carbon atoms are methyl, ethyl, propyl, butyl, pentyl, hexyl, heptyl, octyl, nonyl and decyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A specific group of alkyl residues is formed by the residues methyl, ethyl, n-propyl, isopropyl, n-butyl, isobutyl, sec-butyl and tert-butyl.

As used herein, the term "cycloalkyl" is understood as being a mono- or bicyclic carbon-based ring system, non-limiting examples of which include cyclopropyl, cyclobutyl, cyclopentyl, cyclohexyl and cycloheptyl.

As used herein, the term "acyl" is understood as being a $C_2$-$C_{12}$ acyl group that can be optionally substituted.

As used herein, the term "aryl" is understood as being an aromatic substituent which is a single ring or multiple rings fused together and which may optionally be substituted. The aryl group can be for example a $C_6$-$C_{12}$ aryl group. When formed of multiple rings, at least one of the constituent rings is aromatic. In an embodiment, aryl substituents include phenyl, and naphthyl groups.

The term "substituted" as used herein, means that a hydrogen radical of the designated moiety is replaced with the radical of a specified substituent, provided that the substitution results in a stable or chemically feasible compound. Non-limiting examples of substituents include OH, O-Acyl, O-Alkyl, O-Aryl, aryl, N-Alkyl, halogen (F, Cl, Br, or I).

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 99% of the starting material or substrate is converted to product.

The expression "cardanol or of a derivative thereof" as used herein refers to compounds that have a structure that is similar to cardanol. For example, such compounds can be isomers of cardanol e.g. compounds in which at least one double bond has been isomerized e.g. from a cis to a trans-alkene isomers or other positional isomers. Such derivatives can also comprises known natural derivatives of cardanol that are, for example, anacardic acid, cardol, urushiol, as well as protected versions of these compounds in which at least one OH group or at least one $CO_2H$ group has been protected with a suitable protecting group.

II. Synthesis of Methacrylated Cardanol Glycidyl Ethers

For example, the compounds, intermediates, derivatives, compositions and polymers of the present disclosure can be prepared by using biobased based starting materials from renewable resources (see generic schematic route in Scheme 1A as well as a specific example provided in Scheme 1B with a specific example as starting material). For example, a vegetable oil can be used in the synthesis of the compounds, derivatives, intermediates, compositions and polymers of the present disclosure. For example, compound (I), found in Scheme 1A (for which $R_1$=$R_2$=$R_3$=$R_4$=H i.e. cardanol (1) in Scheme 1B)), can be used as starting material. Cardanol (1) is a by-product of cashew nut industry composed of a mixture of compounds (for example a mixture of at least two structures as those shown in Schemes 1A and 1B. These structures each comprise a phenolic ring that is meta-substituted with a 15 carbons chain length, each structures differing depending on the degrees of unsaturation of the carbon chain (side-chain) as shown in Scheme 1A and 1B. For example, the compounds, intermediates and derivatives of the present disclosure can be prepared by carrying out by introducing a glycidyl unit on compound (I) (for example by reacting cardanol with an oxirane-containing reactive moiety (e.g. epichlorohydrin (see for example compound II obtained), followed by epoxidation of alkenes (see for example compound III obtained) and ring opening of oxiranes (for example opening the oxiranes of the oxirane-containing moiety and/or the oxiranes generated by the epoxidation reaction) with a nucleophilic reagent that comprises at least one polymerizable function or group (for example an organic acid that comprises at least one polymerizable moiety e.g. an unsaturated bond such as a double bond or triple bond). For example, use of methacrylic acid as nucleophilic agent afforded the biobased vinylester monomers as a mixture of compounds IVa and IVb. Compounds IVa and IVb were, for example, diluted in a reactive diluent obtained by esterification of glycerol and methacrylic acid (see compounds 4a and 4b of Scheme 1B). Formulation of this diluted composition was performed as described in polymerization conditions section. Details regarding the synthesis of compounds of formulas IVa and IVb as well as compounds of formulas 4a and 4b are given below in Schemes 1A and 1B and the following pages.

SCHEME 1A
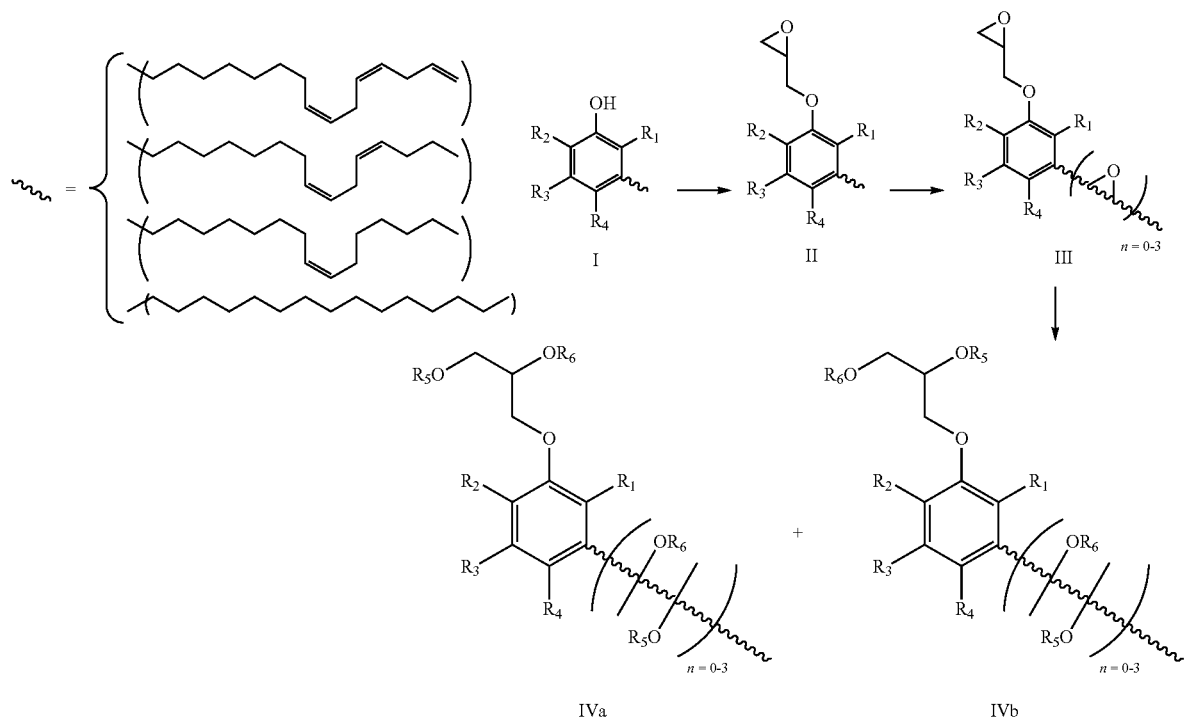
$R_1, R_2, R_3, R_4$ = H, F, Cl, Br, I, OH; O-alkyl; O-aryl; O-acyl; aryl
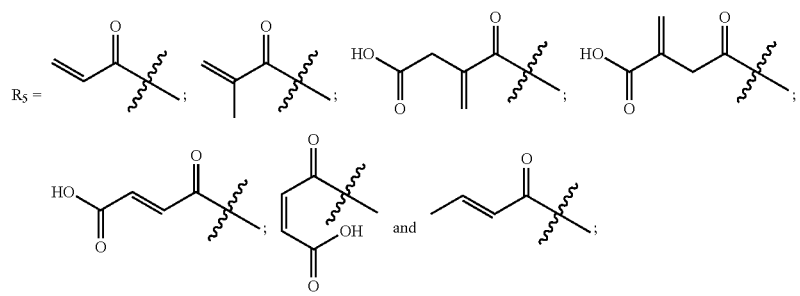
$R_6$ = H, acyl
Scheme 1B
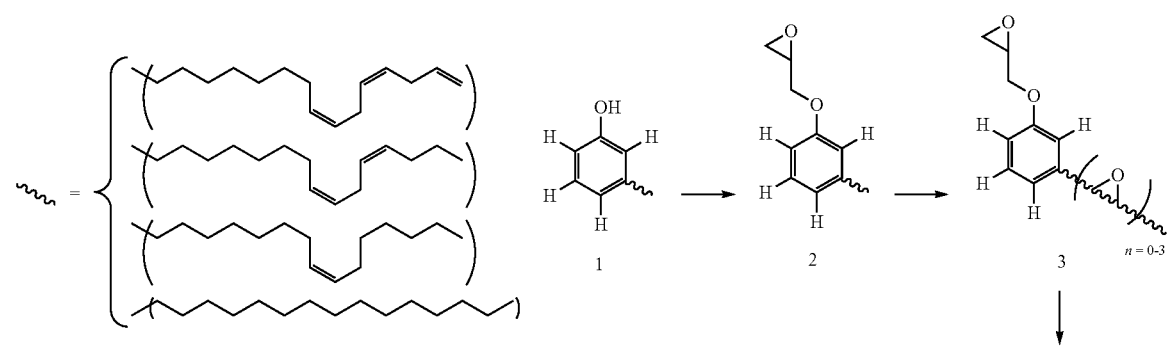

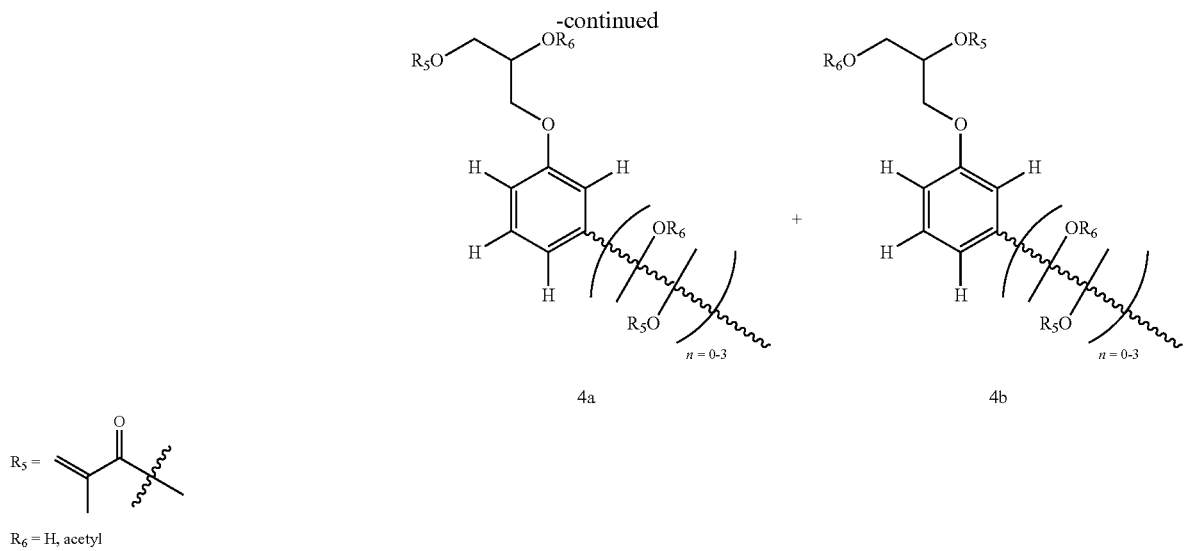

4a + 4b

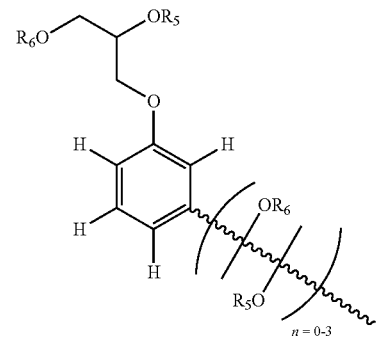

$R_6$ = H, acetyl

Cardanol Glycidyl Ether (2):

In a three-necked flask equipped with a mechanical stirrer, a temperature controller, a heating mantle, an addition funnel and a condenser, 1 kg of cardanol (1) (see Scheme 1B) (301.06 g/mol, 3.3216 mol, 1 eq) and 1.042 L of epichlorohydrin (92.52 g/mol, 13.2864 mole, d=1.18, 4 eq.) were introduced and bring to 100° C. A 40% NaOH solution was added (398.6 g of NaOH in 1 L of water, 40 g/mol, 9.9648 mol, 3 eq.) over a period of 3.5 hours. Heating was continued for an additional 15 minutes after addition of NaOH. The aqueous and organic phases were separated and washed with warm water three times until neutral pH. Epichlorohydrin was evaporated under reduced pressure to provide cardanol glycidyl ether (2) as orange-brown oil quantitatively. The person skilled in the art would understand that various other compounds and derivatives can be prepared by such a method (see compound II in Scheme 1A). For example, simply by replacing the starting material cardanol (1) (see Scheme 1B) by another compound (see the various possibilities for compound I in Scheme 1A), it is possible to obtain various different compounds of formulas II. For example, such starting material can be anacardic acid, cardol, urushiol (see structures below). The person skilled in the art would understand that some modifications of these starting materials can be done such as adding protecting groups etc. In any event, such compounds of formula II, when prepared by using a starting material that is different from cardanol (1), can be referred to as derivatives (or analogs) of cardanol glycidyl ether.

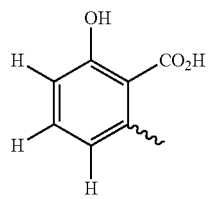

anacardic acid

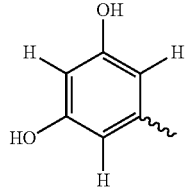

cardol

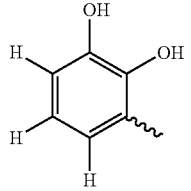

urushiol

Epoxidized Cardanol Glycidyl Ether (3):

In a three-necked flask equipped with a mechanical stirrer, a temperature controller and a heating mantle, heat 1190 g of cardanol glycidyl ether (2) (see Scheme 1B) (3.3325 mole, ~357.09 g/mol, 1 eq.) at 75° C. and add 143 mL of 88% formic acid (3.3325 mol, 46.02 g/mol, d=1.22, 1 eq.) and 1207 ml of $H_2O_2$ 29% (11.6638 mol, 34.01 g/mol, d=1.133, 3.5 eq.). Allow the temperature to rise to 75° C. and control the exotherm so that it will not fall below 70° C. or above 85° C. This step may take more than 2 hours. When the exotherm is completed, set the temperature controller to 75° C. and allow the reaction to react for an additional hour. Subsequently, let the reaction mixture to separate and discard the aqueous phase. Add 1.2 L of toluene, 1.2 L of water and stir 5 minutes at 50° C. Separate liquid phases, remove the aqueous phase and wash again with water two times, one time with saturated $NaHCO_3$ and another time with water. Evaporation of the solvent under reduced pressure yielded 1187 g of epoxidized cardanol glycidyl ether (3) at ~2.6 oxiranes per molecule as an orange-red oil comprising a mixture of compounds that comprise at least two compounds having chains chosen from the following structures:

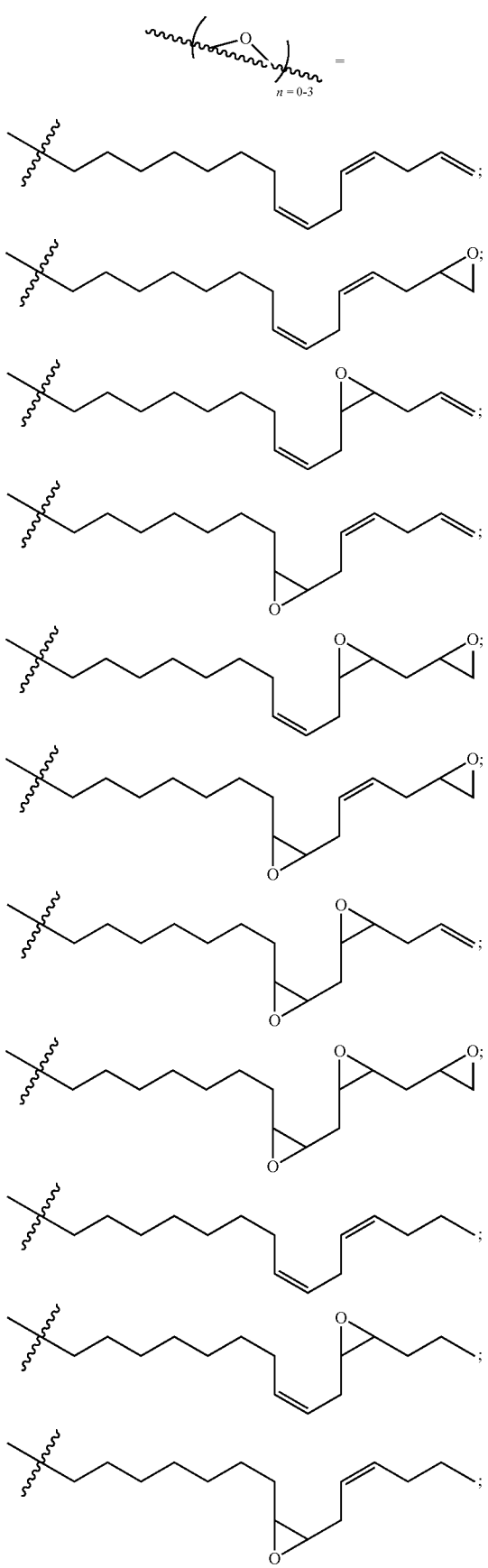

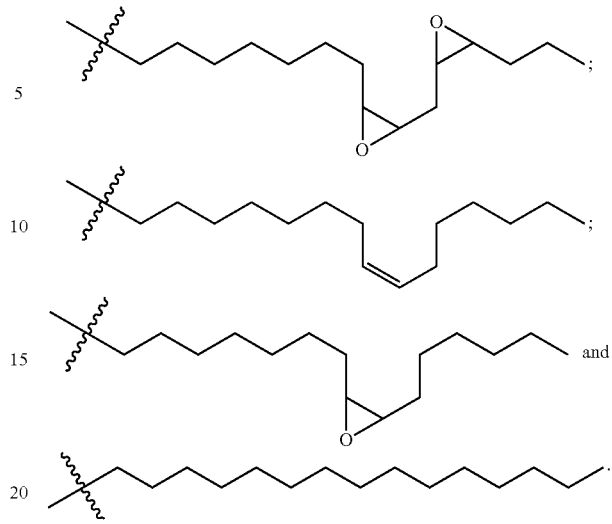

Alternatively, interconversions of cis/trans-alkene isomers and positional isomers can be accomplished (for example with a catalyst such as palladium on carbon) to provide a mixture of regioisomers of cis and/or trans configuration. Accordingly, I' (isomerized cardanol and derivatives thereof) can be transformed by the above methodology until III' as illustrated herein below in Scheme 2.

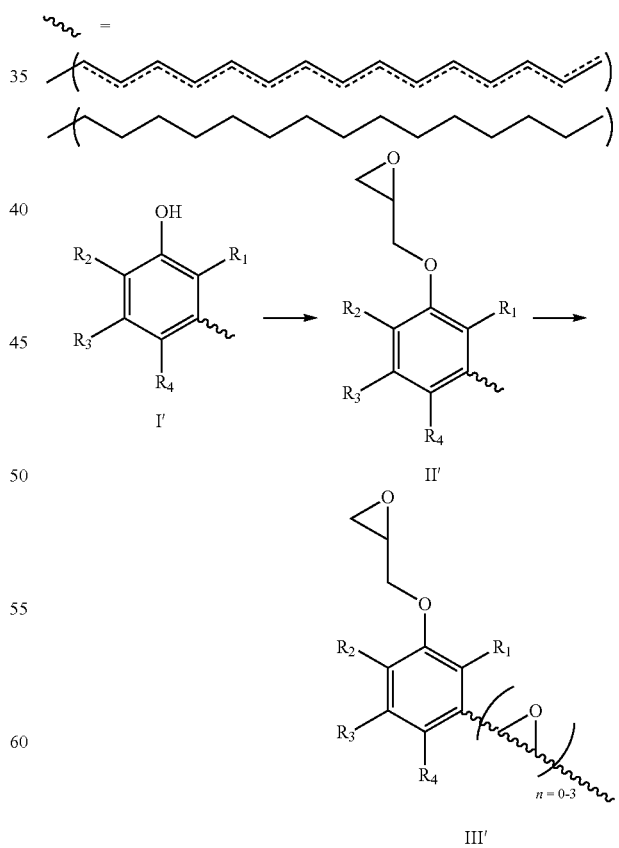

$R_1$, $R_2$, $R_3$, $R_4$ = H, F, Cl, Br, I, OH; O-alkyl; O-aryl; O-acyl

It is also possible to carry out such an isomerization on compound II so as to eventually obtain compound II'. The resulting epoxides III or III' are then transformed to their corresponding methacrylates IV or IV'.

Methacrylated Cardanol Glycidyl Ether (4a and 4b):

In a three-necked flask equipped with a mechanical stirrer, a temperature controller, a heating mantle and an addition funnel, add 1187 g of epoxidized cardanol glycidyl ether (3) (see Scheme 1B) (3.0760 moles, ~385.89 g/mol, 1 eq.), 0.25 g of 4-tert-butylcatechol (100 ppm vs. reagents) and 5.9 mL of HyCat 2000S catalyst (0.1% wt. vs epoxy). Heat to 110° C. and leave for 5 minutes. Add dropwise 1100 mL of methacrylic acid (12.92 mol, 86.06 g/mol, d=1.015, 4.2 eq.) in a period of one hour and let at 110° C. for an additional 4 hours. Let to cool down to room temperature and distillation of residual methacrylic acid provides 1660 g of methacrylated cardanol glycidyl ether (4a and 4b) as a brown viscous liquid that comprises at least two compounds having chains chosen from the following structures:

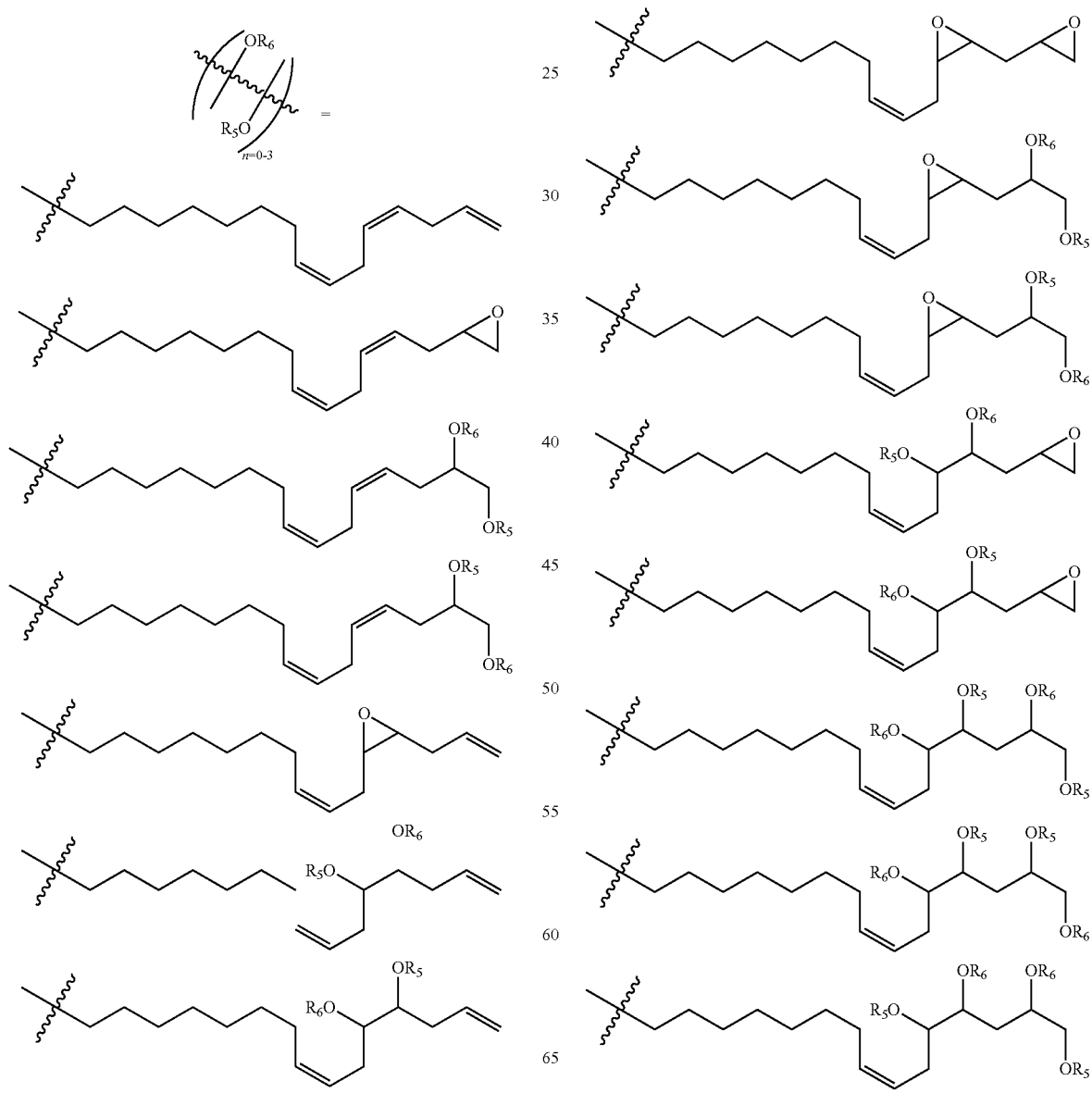

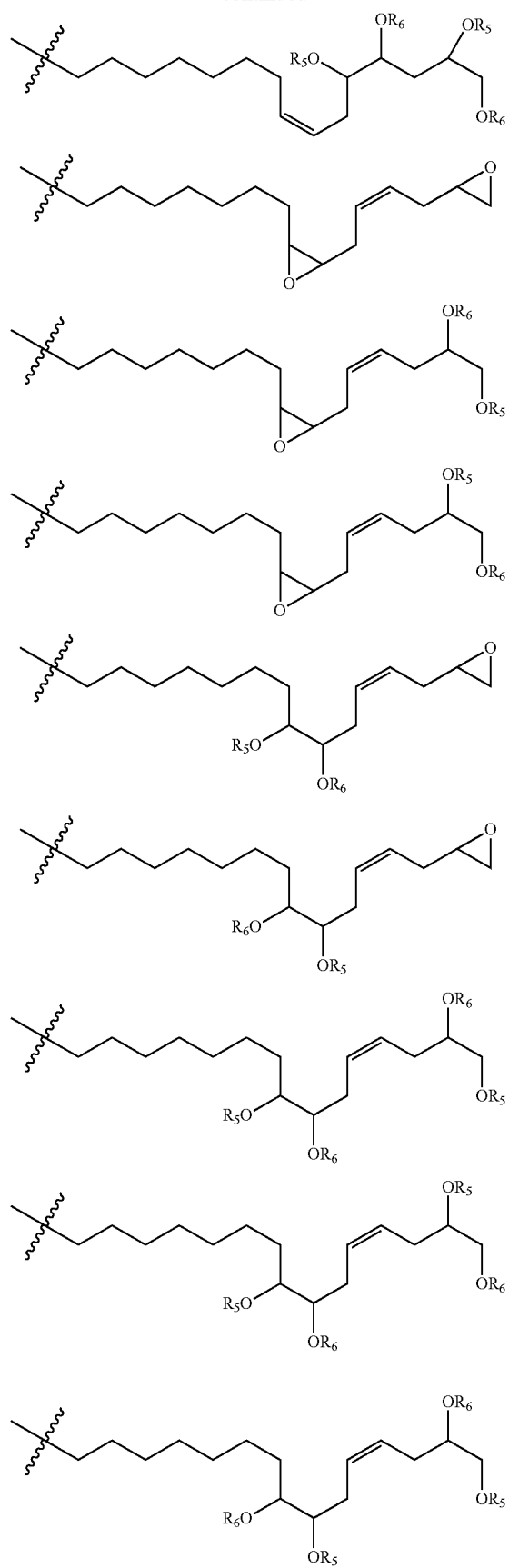
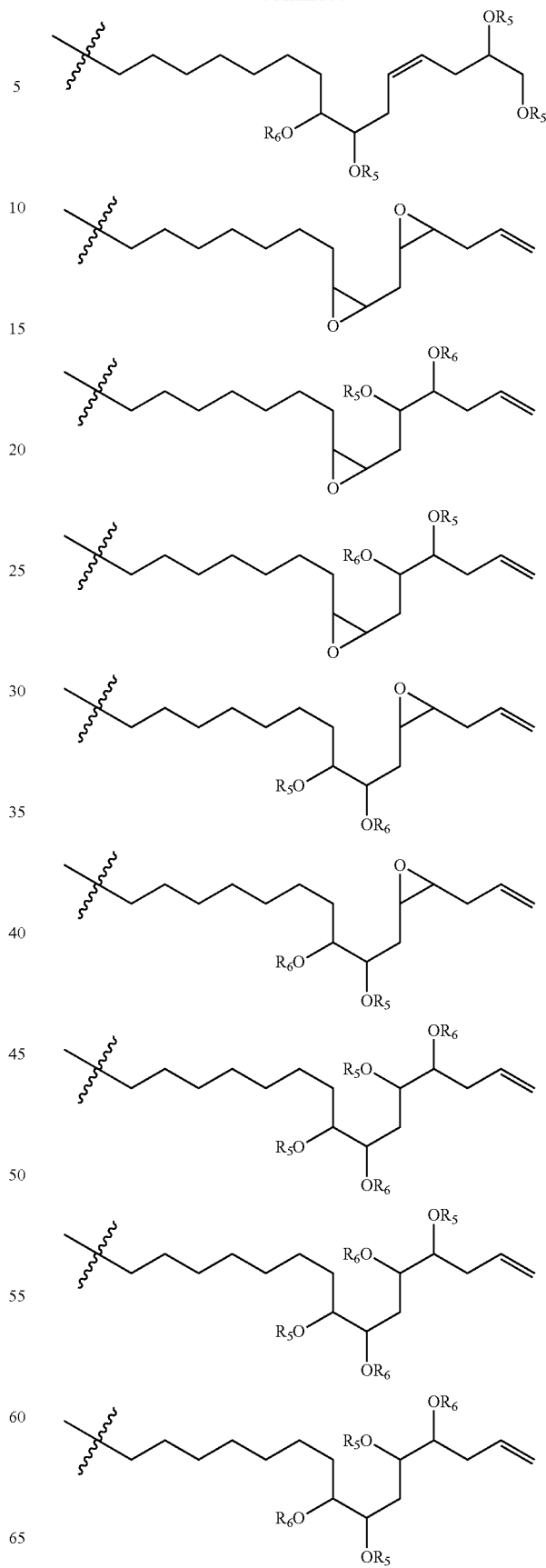

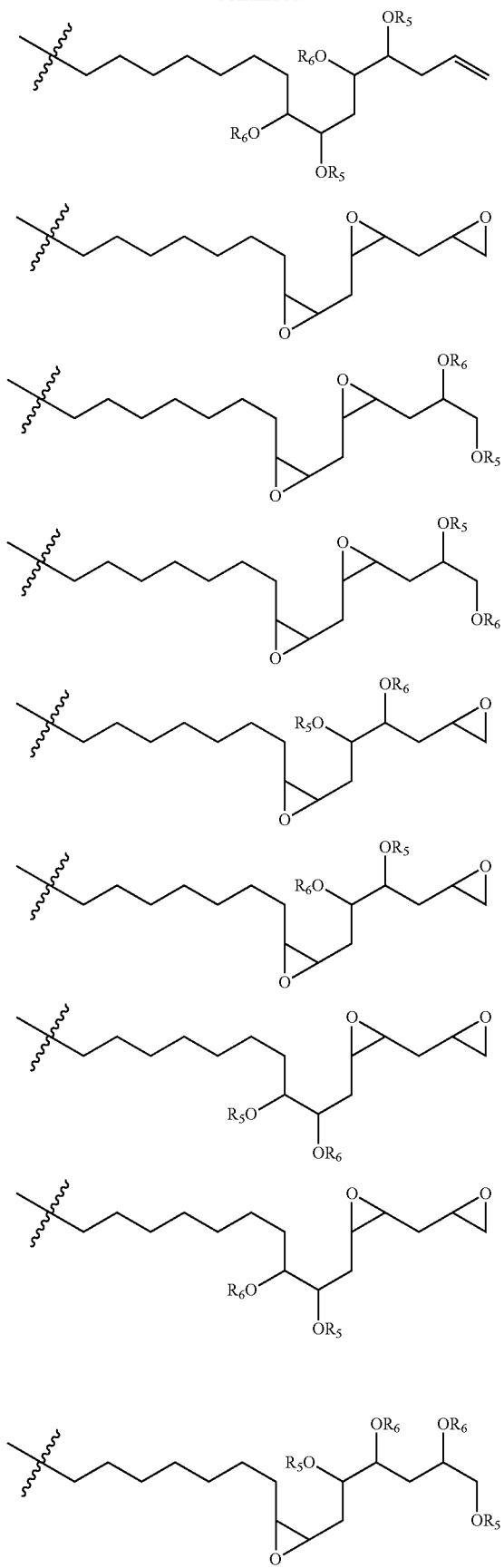
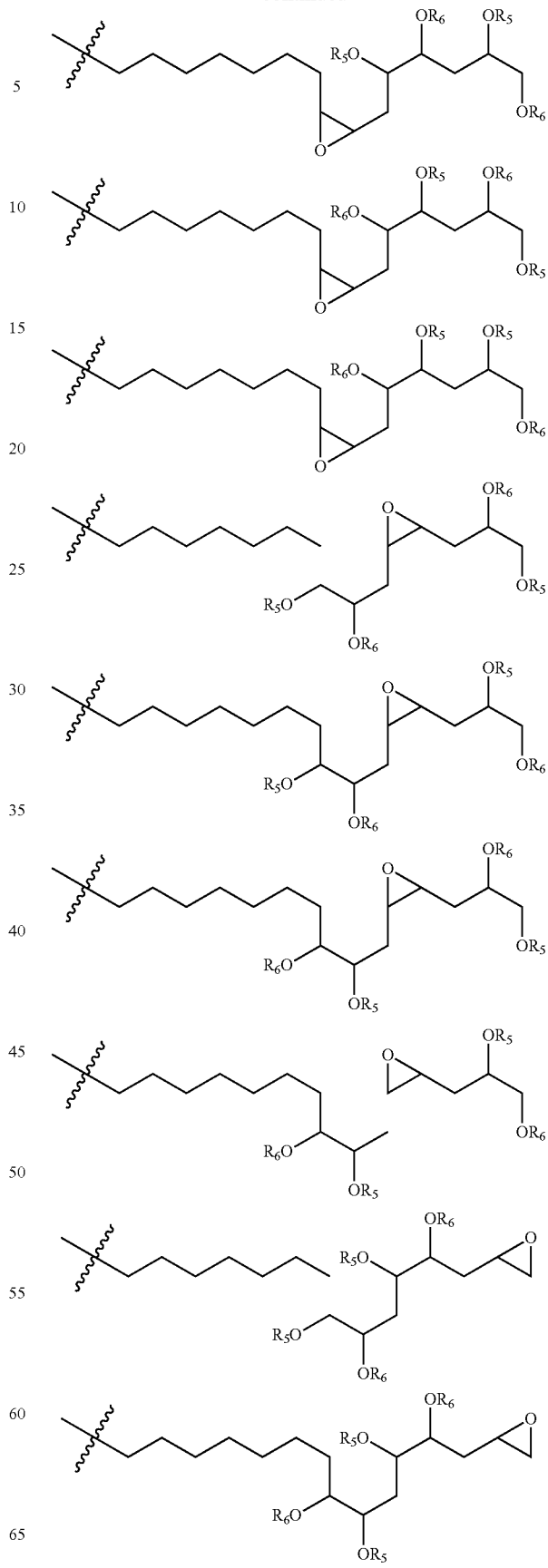

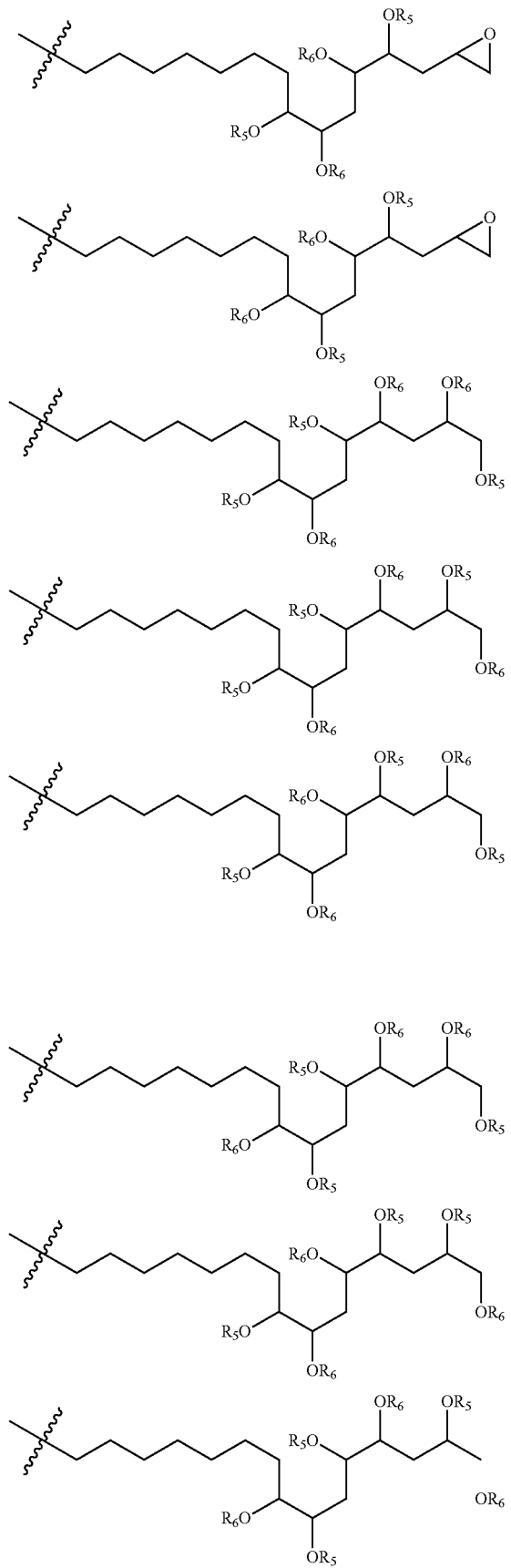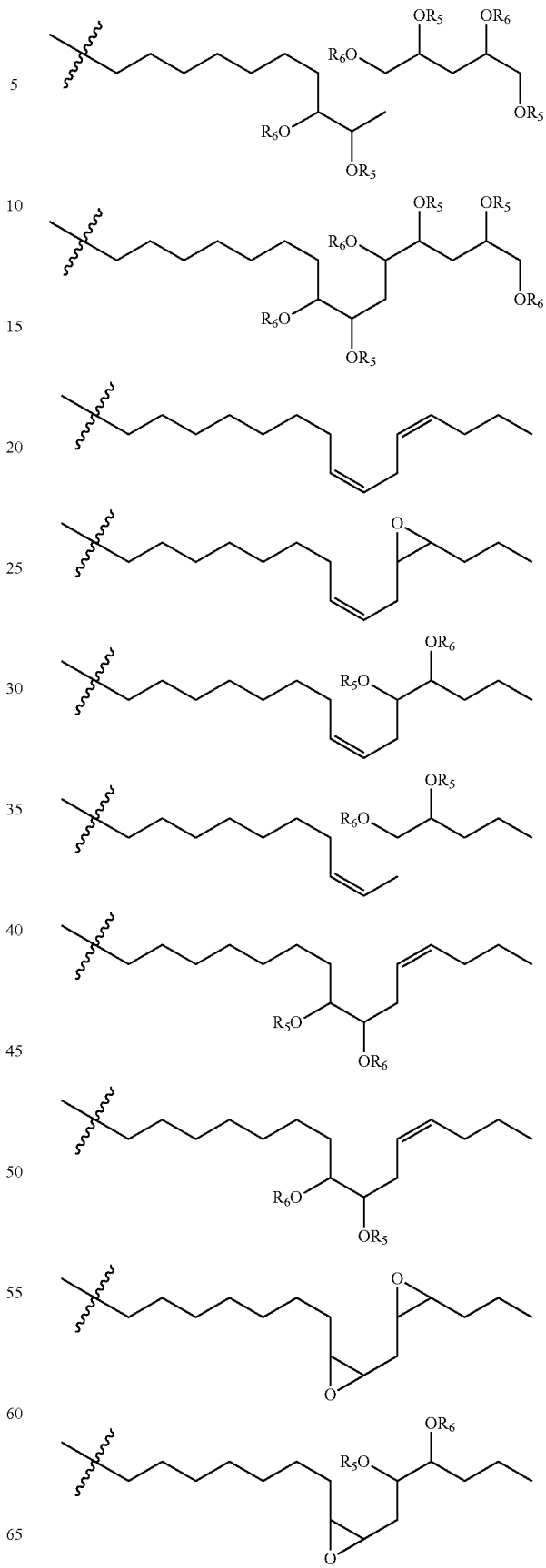

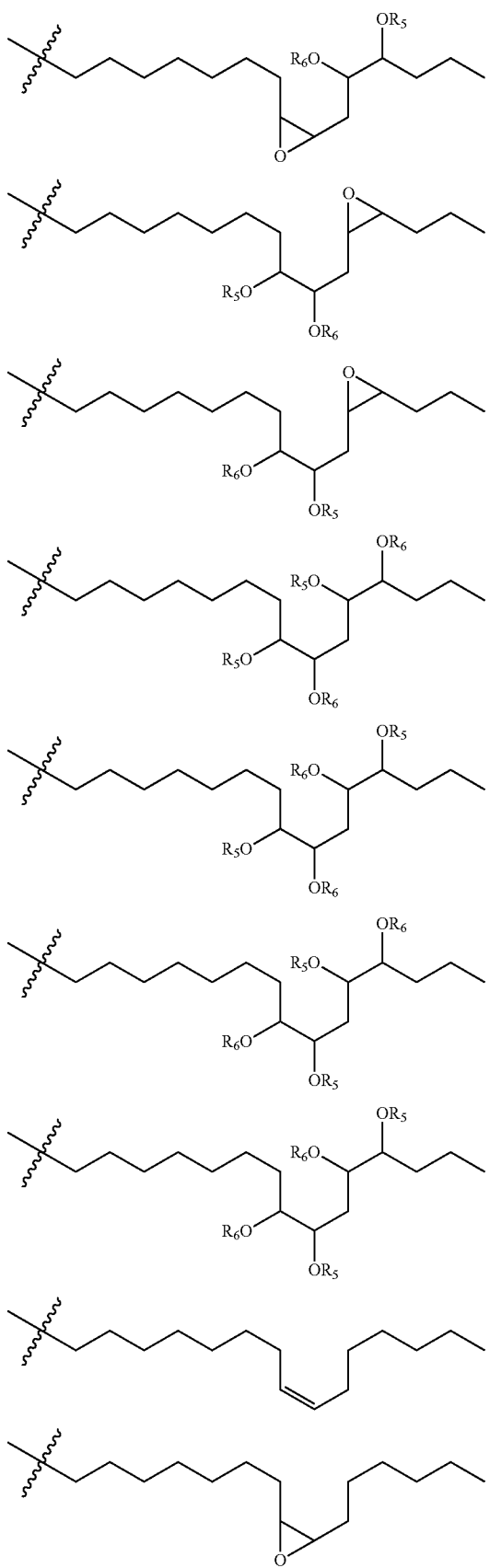
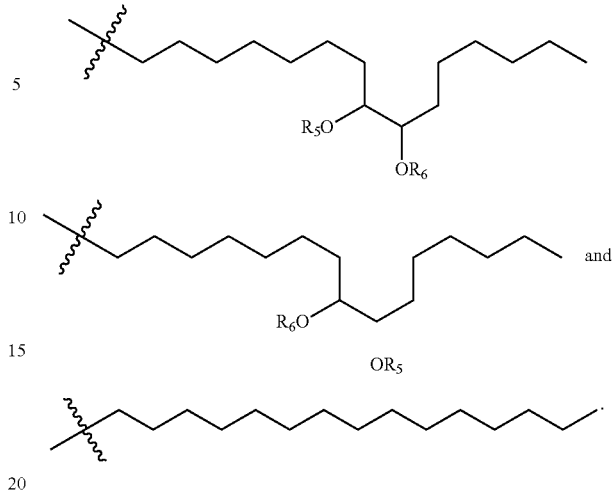

The following step can be achieved in order to reduce resin viscosity: After distillation of methacrylic acid, heat at 110° C., add 872 mL of acetic anhydride (9.2280 mol, 102.09 g/mol, d=1.08, 3 eq.) and allow to react one hour. Note that any anhydrides can be used such as acetic anhydride, methacrylic anhydride etc. The following procedure involves the use of acetic anhydride. Pour ice to cool down the reaction and to neutralize excess of acetic anhydride. After 10 minutes, add slowly 900 mL of cold NaOH 10M and allow to neutralize 5 minutes. Separate the layers and discard the aqueous phase. Add 1.5 L of EtOAc and wash with saturated $NaHCO_3$ until neutral pH. Evaporation of solvent provides ~1380 g of acetylated methacrylated glycidyl ether of cardanol as a viscous brown resin.

III. Synthesis of Reactive Diluents

In an example, the present disclosure relates to glycerol methacrylate as a reactive diluent. Other reactive diluents that can be used. For example, they can be, but not limited to: styrene and all styrenic monomers (i.e. methylstyrene and the like), divinylbenzene and derivatives, acrylic acid and related esters, methacrylic acid and related esters and vinylic esters such as vinyl acetate. The preparation of glycerol methacrylate in accordance with an example of the present disclosure is illustrated in Scheme 3.

Scheme 3

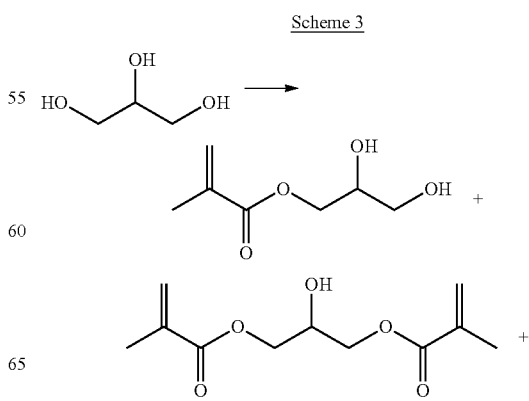

-continued

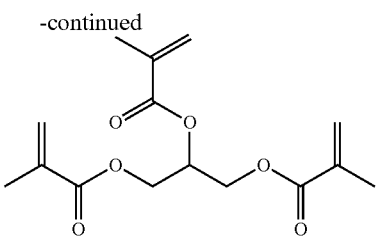

Glycerol Methacrylate:

In a three-necked flask equipped with a mechanical stirrer, a temperature controller and a heating mantle, incorporate 1000 g of glycerol (92.09 g/mol, 10.8589 mole, d=1.26, 1 eq.), 3683 mL of methacrylic acid (43.4358 mol, 86.06 g/mol, d=1.015, 4 eq.), 37.4 g of p-toluene sulfonic acid (0.2172 mol, 172.20 g/mol, 0.02 eq.), 500 mg of hydroquinone and heat at 90° C. overnight. Distill residual methacrylic acid without exceeding 90° C. to provide crude glycerol methacrylate. Then, dilute with 1 L of EtOAc and wash three times with water to remove excess of glycerol and monomethacrylates. Evaporation of solvent gives glycerol methacrylate as a yellowish liquid.

For example, the reactive diluent can comprise at least one compound chosen from

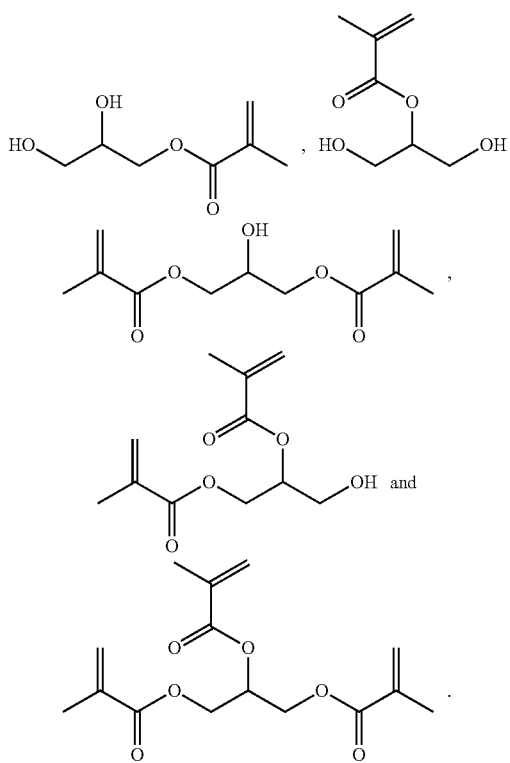

IV. Polymerization Conditions

The samples obtained from the compounds 4a and 4b were combined with a reactive diluent (glycerol methacrylate) to obtain a composition. The viscosities of such compositions were adjusted with appropriate amounts of the reactive diluent. Other components have also been added to these compositions i.e. formulated with a defoamer and promoted. The formulated compositions were cast into a mold or laminated (reinforced) to yield the desired polymers. All of the samples were heat cured ranging from 40 to 100° C. using different types of catalysts (1.25% to 3%) and accelerators (promoters) in many different proportions (0.05 to 0.3%). Compositions can be catalysed by hydroperoxydes, ketone peroxides, diacyl peroxydes and activated with cobalt derivatives such as cobalt naphthenate or cobalt 2-ethylhexanoate and/or aniline derived compounds non-limiting examples of which include dimethylaniline or diethylaniline. The following physical and mechanical properties were measured on two types of samples (cast & laminated): Brookfield viscosity, tensile properties (ASTM D638) and flexural properties (ASTM D792).

A typical formulation of the biobased vinyl ester is as follow: 50 g of 4 is mixed with 50 g of glycerol methacrylate, followed by 0.5% of Schweggo 6377 (defoaming agent), 0.11% of Cobalt Naphthenate and 0.1% (promoter) of DMA (dimethylaniline) (promoter). The resulting resin is then catalyzed with 3% of Luperox DHD-9 (methyl ethyl ketone peroxide) (catalyzer).

IVa. Processing and Applications

The compounds, derivatives, intermediates, compositions and polymers according to the present disclosure exhibit properties, depending on the cure time, cure temperatures and viscosity values making them suitable for use in many practical processes and applications: Hand lay-up process, hand spray up process, RTM (resin transfer molding) process, prepregs and SMC, compression molding and vacuum bagging. In particular, the compounds, derivatives, intermediates, compositions and polymers according to the disclosure is suitable for the following applications but not limited to: Baths and showers, automobile and truck parts, aerospace industry, RV and boat components, swimming pool panels, sports equipment, household equipment.

IVb. Sample Preparation (Hand Lay-Up)

Samples used for mechanical testing were from a plaque. The 15"×18" plaque used to fabricate the samples was hand laminated using the hand lay-up process. The catalyzed resin was prepared by adding 3% (w/w) of Luperox DHD-9 catalyst. Each layer of mat was soaked with a predetermined quantity of resin representing 60% resin and 40% fiber (w/w). A total of three mats were laminated on top of each other for a plaque of approximately 2.2 mm in thickness. An optimum laminating was performed to ensure that no air bubbles were present. The laminating was performed on a Mylar film to give us the option of oven curing. After laminating the plaque, it was placed in an oven at 85° C. for a total of 3 hours. Five days later the test samples were extracted from the plaque using a CNC machine. Type 1 samples according to ASTM D638 were machined for the tensile testing. Rectangular bars of 12.7 mm×2.2 mm and 100 mm in length were machined for ASTM D790 flexural tests.

IVc. Sample Preparation (Cast)

Samples used for mechanical testing were cast directly into an aluminum/silicone mold directly to the shape as per each corresponding ASTM standard. The catalyzed polymer was prepared by adding 3% (w/w) of Luperox DHD-9 catalyst. It was then poured in the mold cavities. The mold was placed in an oven at 85° C. for three hours. The samples were left to cool for a minimum of 2 hours and demolded.

The results obtained for cast polymers (Table 1 herein below) were lower than for a conventional unsaturated polyester resin (AOC C668-T) (see Table 3). However, once the resin was reinforced with mat (Table 2 herein below), better results were obtained than the same conventional unsaturated polyester resin that was used as a comparison.

TABLE 1

Results of casted polymers of the present disclosure

| Tests | Results |
| --- | --- |
| Brookfield viscosity (spindle 4) | ~600 cPs |
| Tensile stress (MPa) | 22 |
| Tensile Modulus (MPa) | 5439 |
| Tensile elongation (%) | 0.6 |
| Flexural stress (MPa) | 93 |
| Flexural Modulus (MPa) | 4844 |
| Flexural elongation (%) | 4.0 |

The results represent the maximum obtained from multiple series of tests.

TABLE 2

Results of fiberglass reinforced polymers of the present disclosure

| Tests | Results* |
| --- | --- |
| Brookfield viscosity (spindle 4) | ~600 cPs |
| Tensile stress (MPa) | 111 (±9) |
| Tensile Modulus (MPa) | 9300 (±2400) |
| Tensile elongation (%) | 2.3 (±0.1) |
| Flexural stress (MPa) | 206 (±12) |
| Flexural Modulus (MPa) | 7005 (±309) |
| Flexural elongation (%) | 3.9 (±0.1) |

The results represent the average and standard deviation of 5 samples in one series of tests. *The above results were obtained from samples reinforced with 60% resin (w/w) and 40% (w/w) continuous filament E-glass mat of random orientation.

TABLE 3

Unsaturated polyester resin AOC C668-T

| Tests | Cast resin[1] | Reinforced resin[2] |
| --- | --- | --- |
| Tensile stress (MPa) | 24 (±9) | 130 (±7) |
| Tensile Modulus (MPa) | 3370 (±545) | 6670 (±425) |
| Tensile elongation (%) | 0.7 (±0.4) | 2.3 (±0.1) |
| Flexural stress (MPa) | 77 (±13) | 181 (±24) |
| Flexural Modulus (MPa) | 2710 (±166) | 5120 (±1010) |
| Flexural elongation (%) | 2.9 (±0.6) | 4.7 (±0.6) |

The results represent the average and standard deviation of 5 samples in one series of tests.
[1] The above results were obtained from samples made from casted resin without any reinforcement.
[2] The above results were obtained from samples reinforced with 60% resin (w/w) and 40% (w/w) continuous filament E-glass mat of random orientation.

V. Synthesis of Methacrylated Cardanol Diglycidyl Ethers

The preparation of methacrylated cardanol diglycidyl ether (7) is illustrated hereinbelow in Scheme 4B. Compound 7 was made by using cardanol as starting material. A more generic synthetic route is also presented in Scheme 4A.

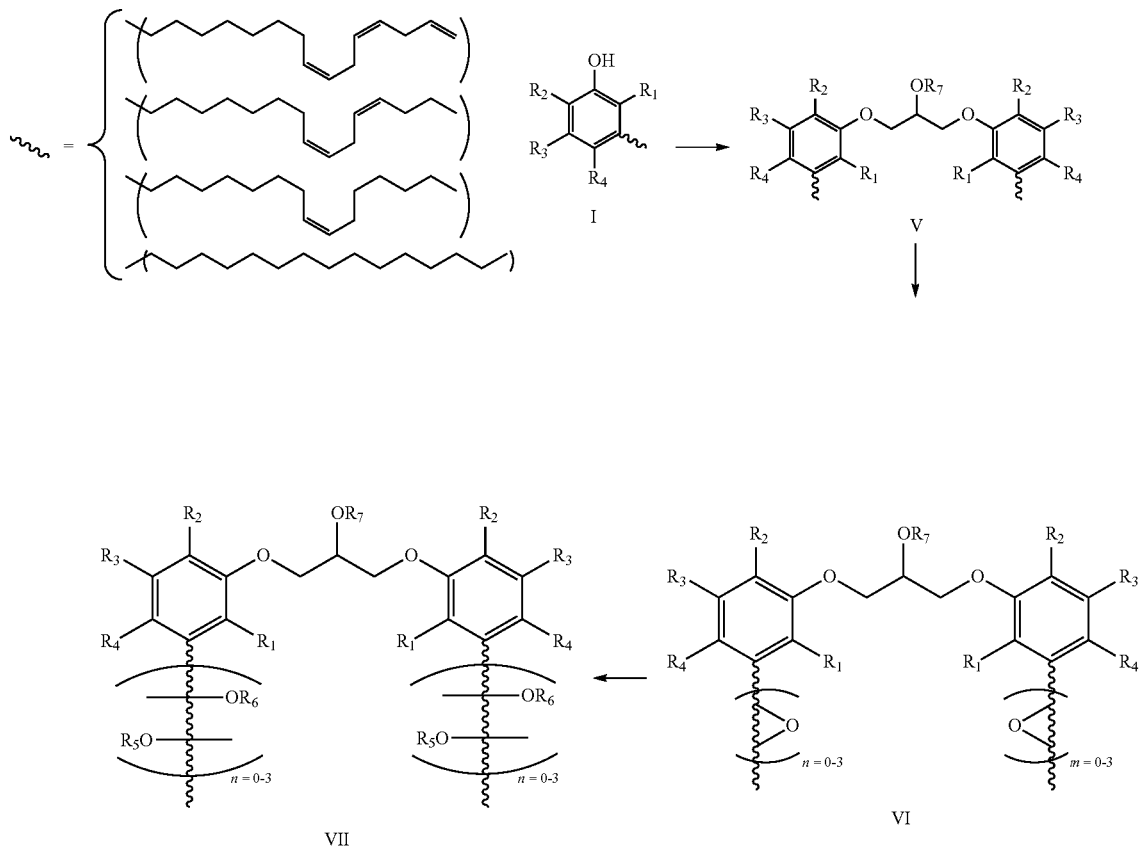

Scheme 4A

-continued $R_1, R_2, R_3, R_4$ = H, F, Cl, Br, I, OH; O-alkyl; O-aryl; O-acyl; aryl

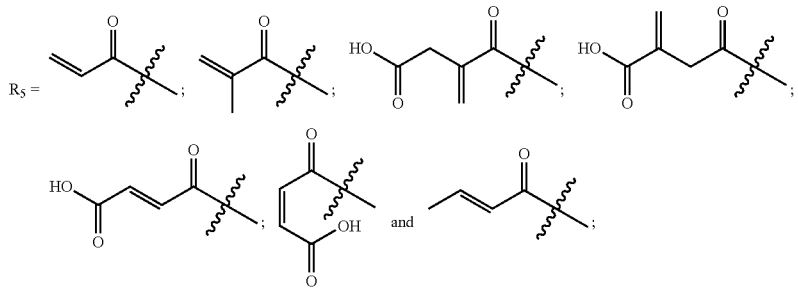

$R_6$ = H, acyl
$R_7$ = H, alkyl, aryl, acyl

Scheme 4B

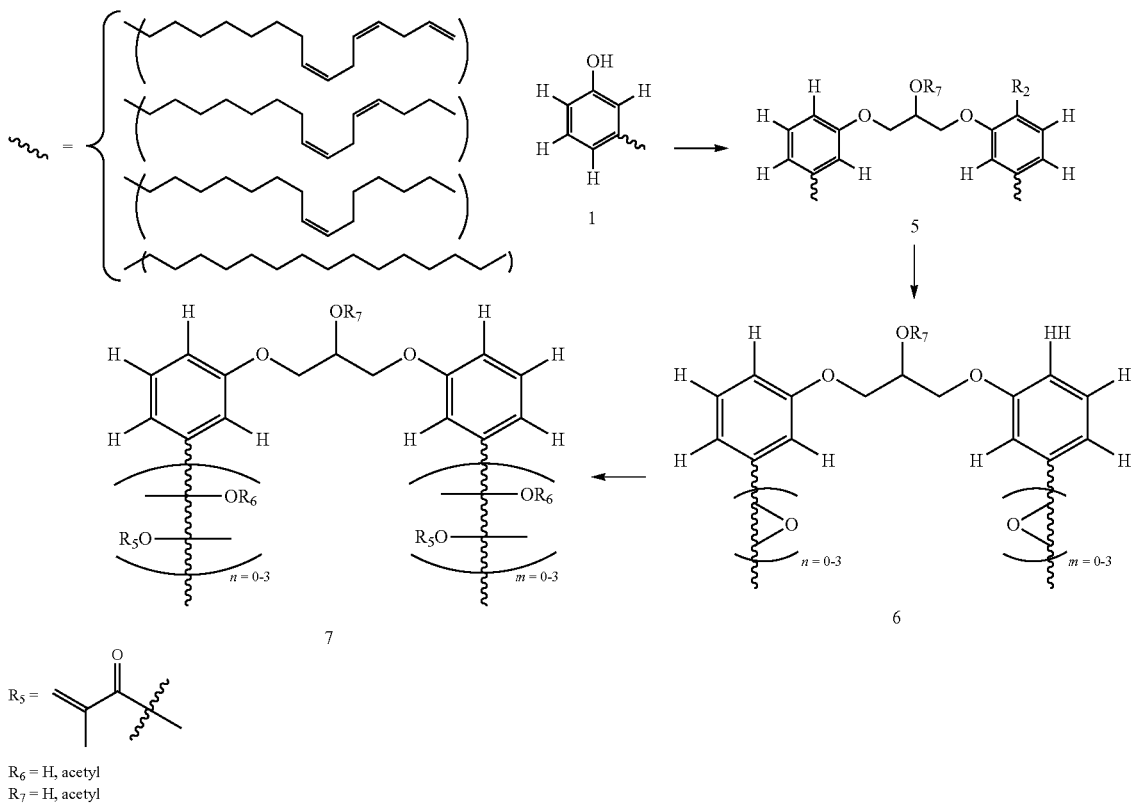

$R_6$ = H, acetyl
$R_7$ = H, acetyl

Glycidyl Diether of Cardanol (5):

1000 g of cardanol (1) (see Scheme 4B) (301.06 g/mol, 3.3216 mol, 1 eq) is dissolved in 1700 mL of acetone. A 4M NaOH solution (136 g NaOH in 850 mL of water, 40 g/mol, 3.4000 mol, 1.025 eq.) and 153 g (130 mL) of epichlorohydrin (92.52 g/mol, 1.6537 mole, d=1.18, 0.5 eq.) were added and refluxed 120 minutes. Then, 250 mL of saturated $NH_4Cl$ was added, acetone was evaporated and the reaction mixture was diluted with ethyl acetate. The two phases were separated and washed with water 3 times (or until neutral pH). Evaporation of ethyl acetate under reduced pressure provided 1081 g of glycidyl diether of cardanol (~90%) as a dark brown oil.

Epoxidized Cardanol Glycidyl Diether (6):

In a three-necked flask equipped with a mechanical stirrer, a temperature controller and a heating mantle, heat 1000 g of cardanol glycidyl diether (5) (see Scheme 4B) ((1.5193 mole, 658.19 g/mol, 1 eq.) at 75° C. and add 126 mL of 88% formic acid (3.3425 mole, 46.02 g/mol, d=1.22, 2.2 eq.) and 1207 ml of $H_2O_2$ 29% (9.5717 mole, 34.01 g/mol, d=1.133, 6.3 eq.). Allow the temperature to rise to 75° C. and control the exotherm so that it will not fall below 70° C. or above 85° C. This step may take more than 2 hours. When the exotherm is completed, set the temperature controller to 75° C. and allow the reaction to react for an additional hour. Subsequently, let the reaction mixture to separate and discard the aqueous phase. Add 1.0 L of ethyl acetate, 1.0 L of water and stir 5 minutes at 60° C. Separate liquid phases, remove the aqueous phase and wash again with water two times, one time with saturated NaHCO₃ and another time with water. Evaporate solvent under reduced pressure to provide 1078 g of epoxidized cardanol diglycidyl ether (6) as an orange-red oil comprising at least two compounds having chains chosen from the following structures in which:

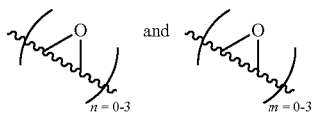

are independently chosen from

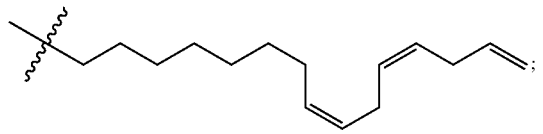

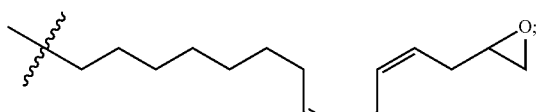

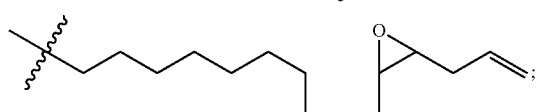

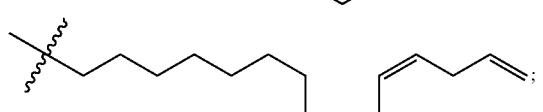

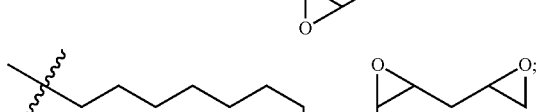

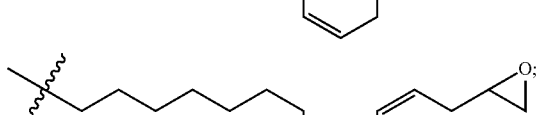

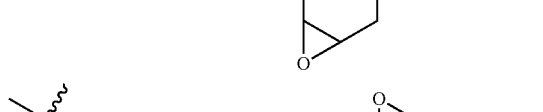

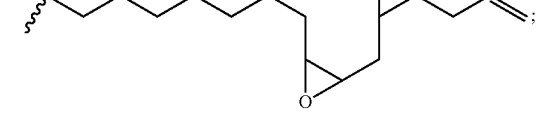

-continued

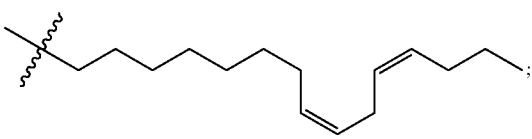

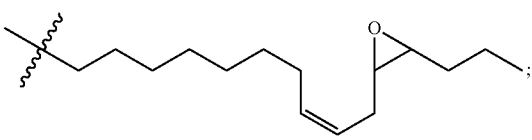

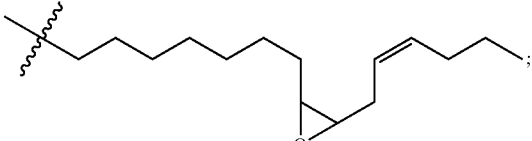

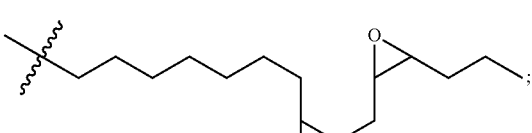

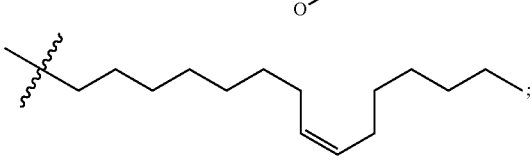

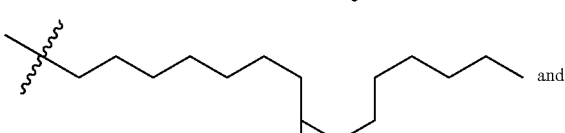

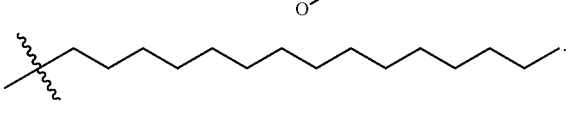

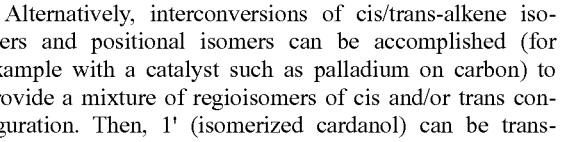

Alternatively, interconversions of cis/trans-alkene isomers and positional isomers can be accomplished (for example with a catalyst such as palladium on carbon) to provide a mixture of regioisomers of cis and/or trans configuration. Then, 1' (isomerized cardanol) can be transformed by the above methodology until 6' as described herein below in Scheme 5.

Scheme 5

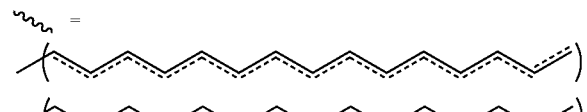

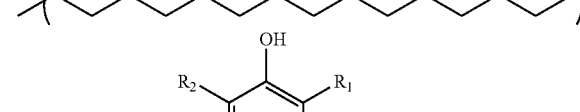

-continued

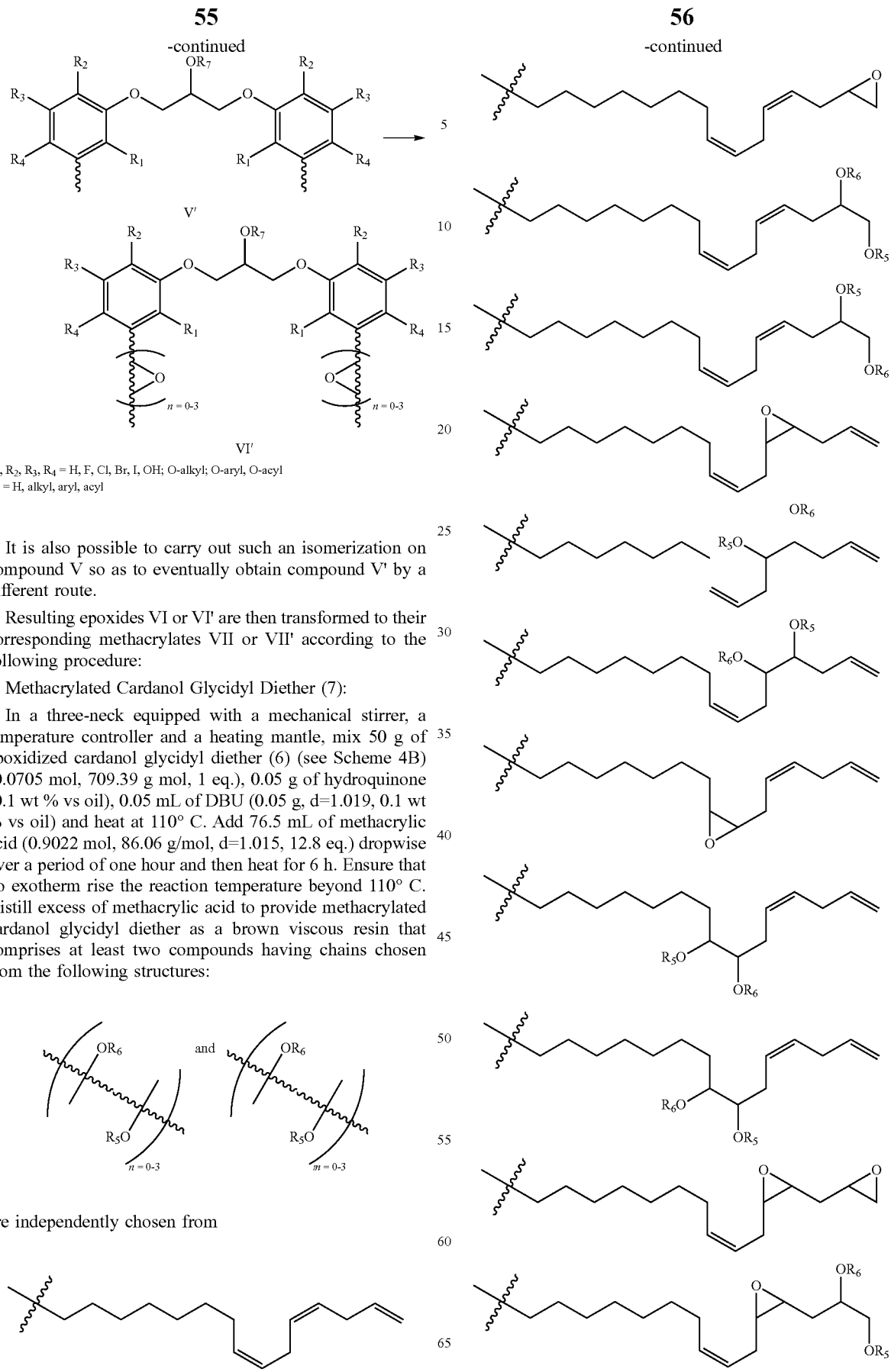

R₁, R₂, R₃, R₄ = H, F, Cl, Br, I, OH; O-alkyl; O-aryl, O-acyl
R₇ = H, alkyl, aryl, acyl It is also possible to carry out such an isomerization on compound V so as to eventually obtain compound V' by a different route.

Resulting epoxides VI or VI' are then transformed to their corresponding methacrylates VII or VII' according to the following procedure:

Methacrylated Cardanol Glycidyl Diether (7):

In a three-neck equipped with a mechanical stirrer, a temperature controller and a heating mantle, mix 50 g of epoxidized cardanol glycidyl diether (6) (see Scheme 4B) (0.0705 mol, 709.39 g mol, 1 eq.), 0.05 g of hydroquinone (0.1 wt % vs oil), 0.05 mL of DBU (0.05 g, d=1.019, 0.1 wt % vs oil) and heat at 110° C. Add 76.5 mL of methacrylic acid (0.9022 mol, 86.06 g/mol, d=1.015, 12.8 eq.) dropwise over a period of one hour and then heat for 6 h. Ensure that no exotherm rise the reaction temperature beyond 110° C. Distill excess of methacrylic acid to provide methacrylated cardanol glycidyl diether as a brown viscous resin that comprises at least two compounds having chains chosen from the following structures:

are independently chosen from

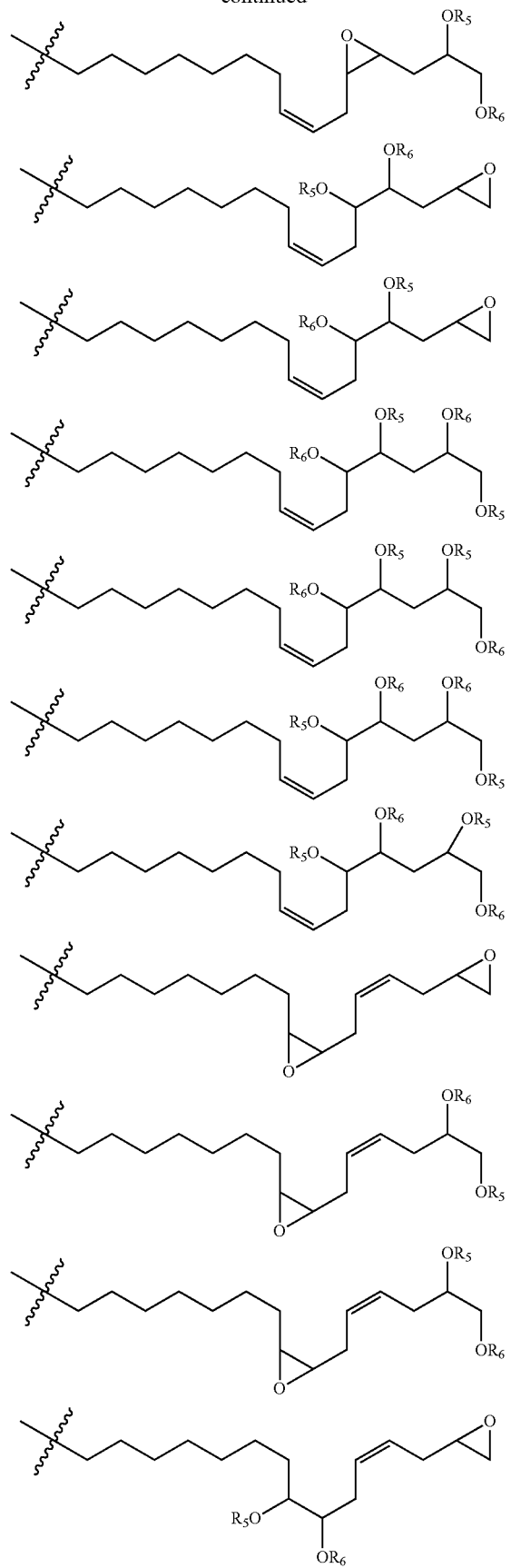
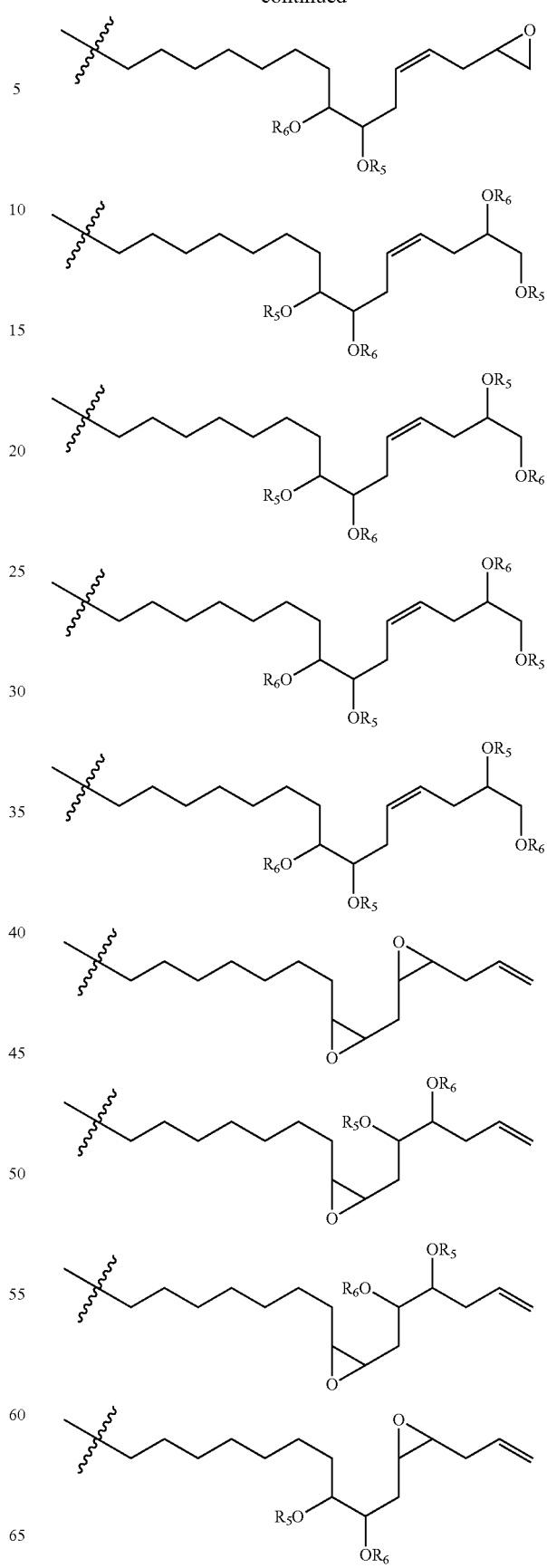

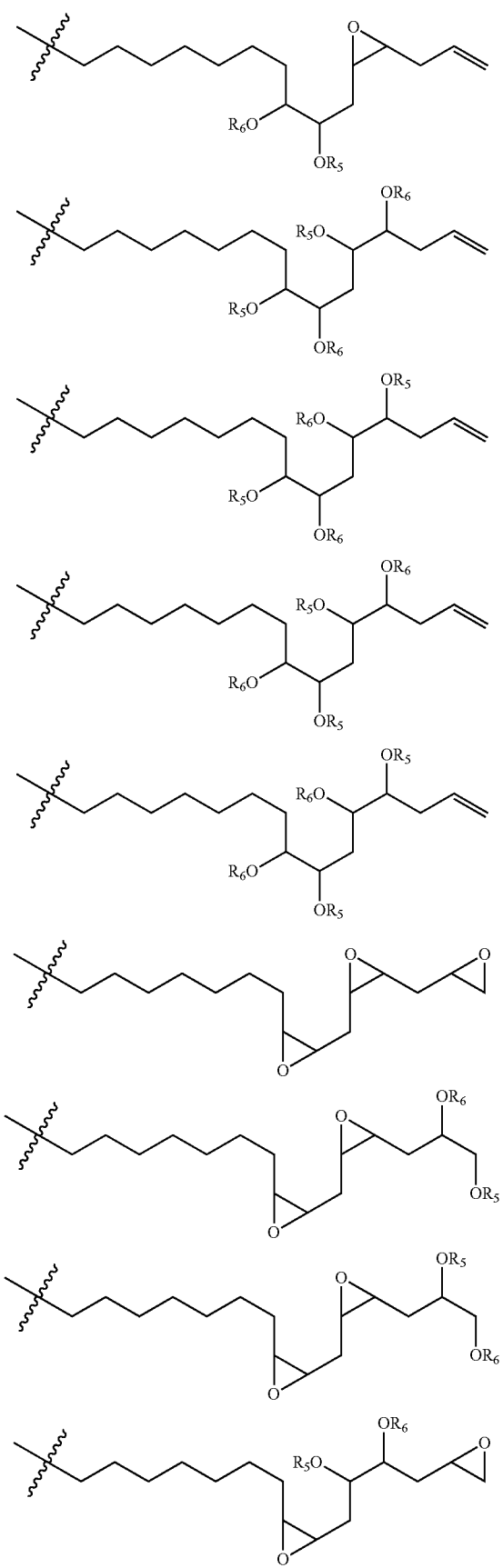
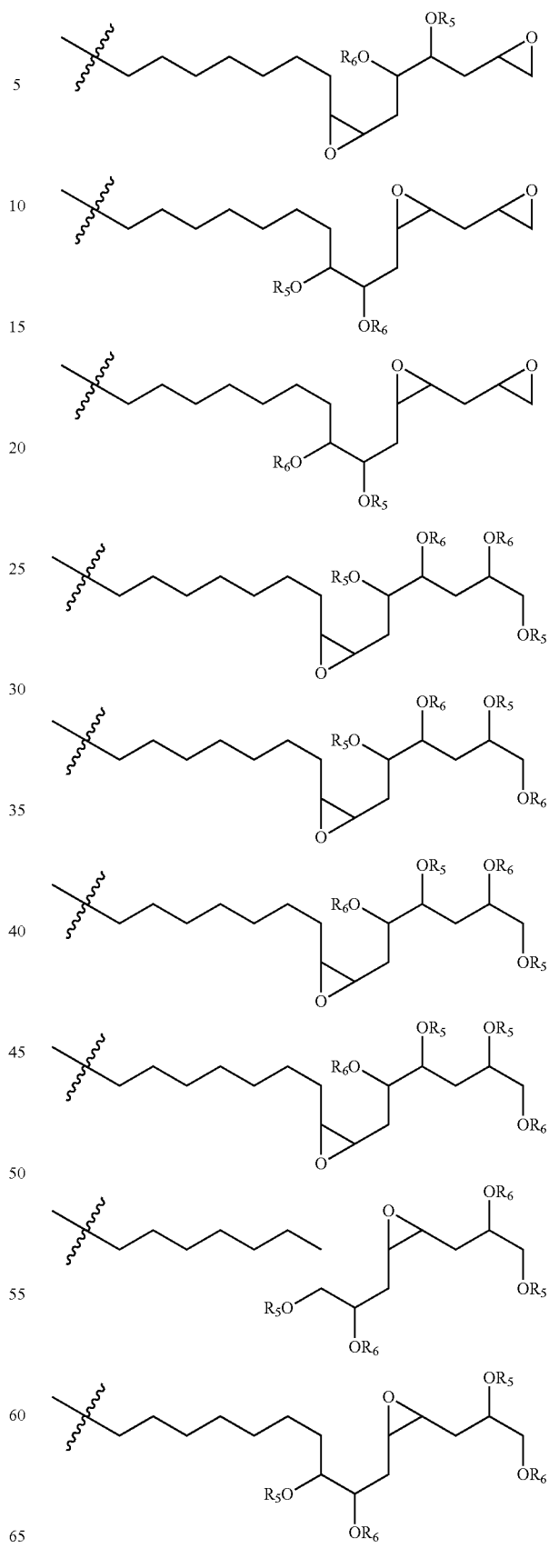

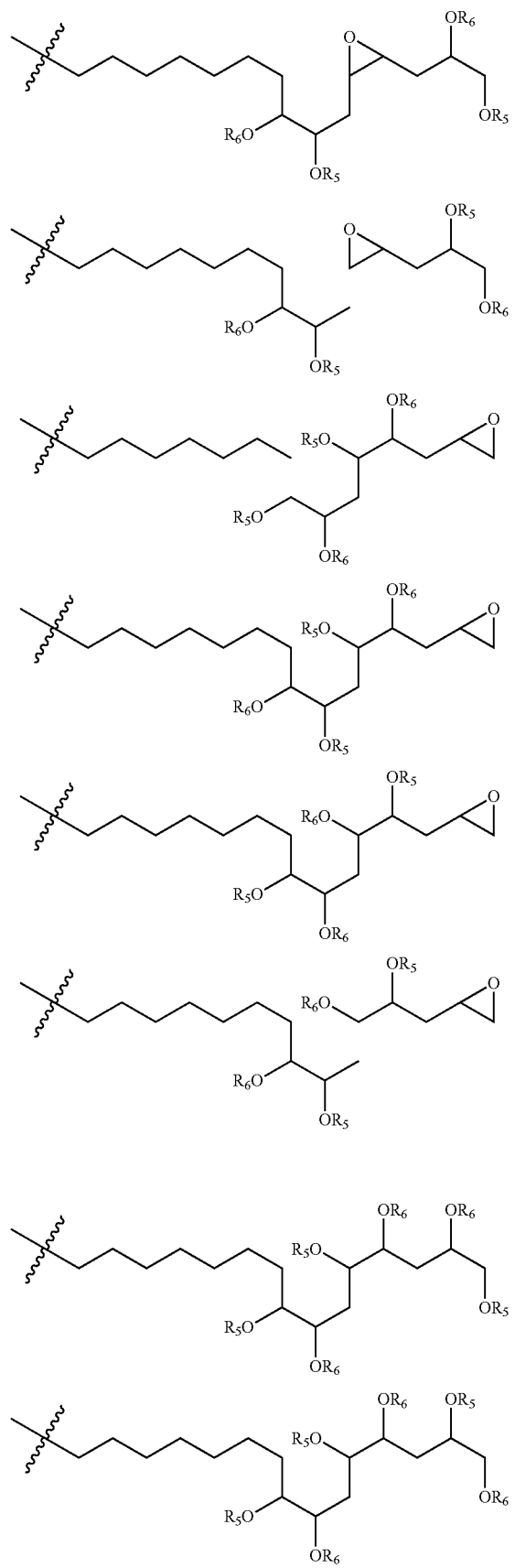
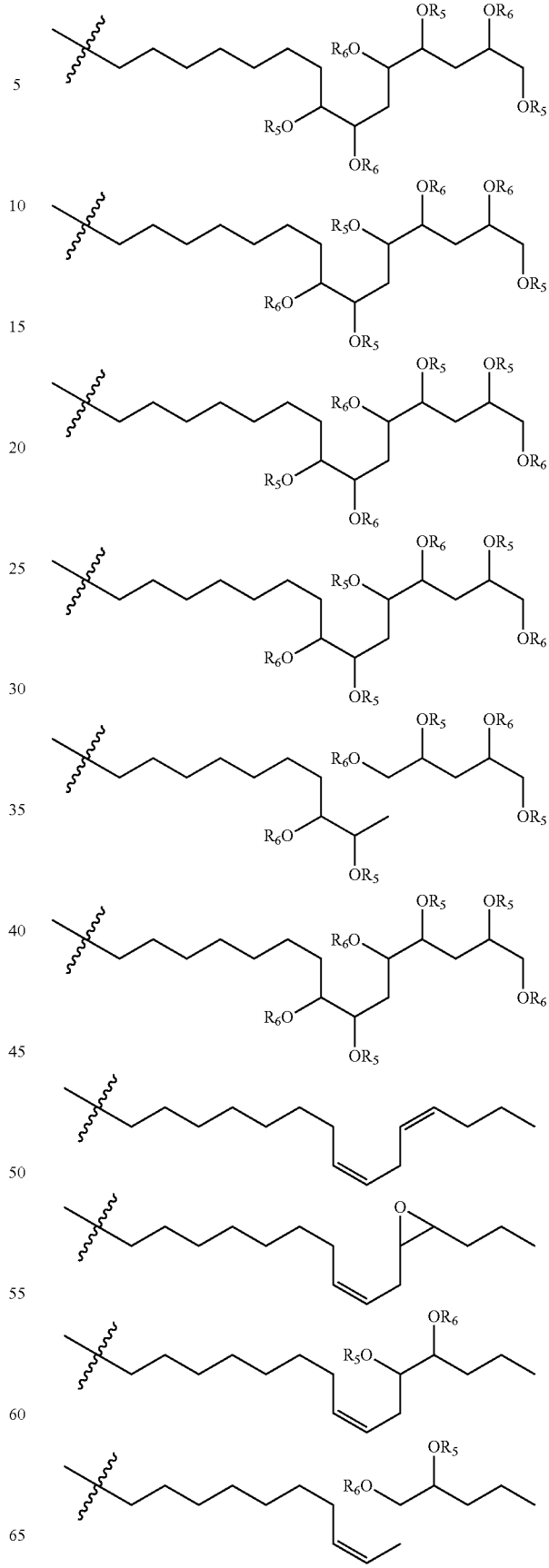

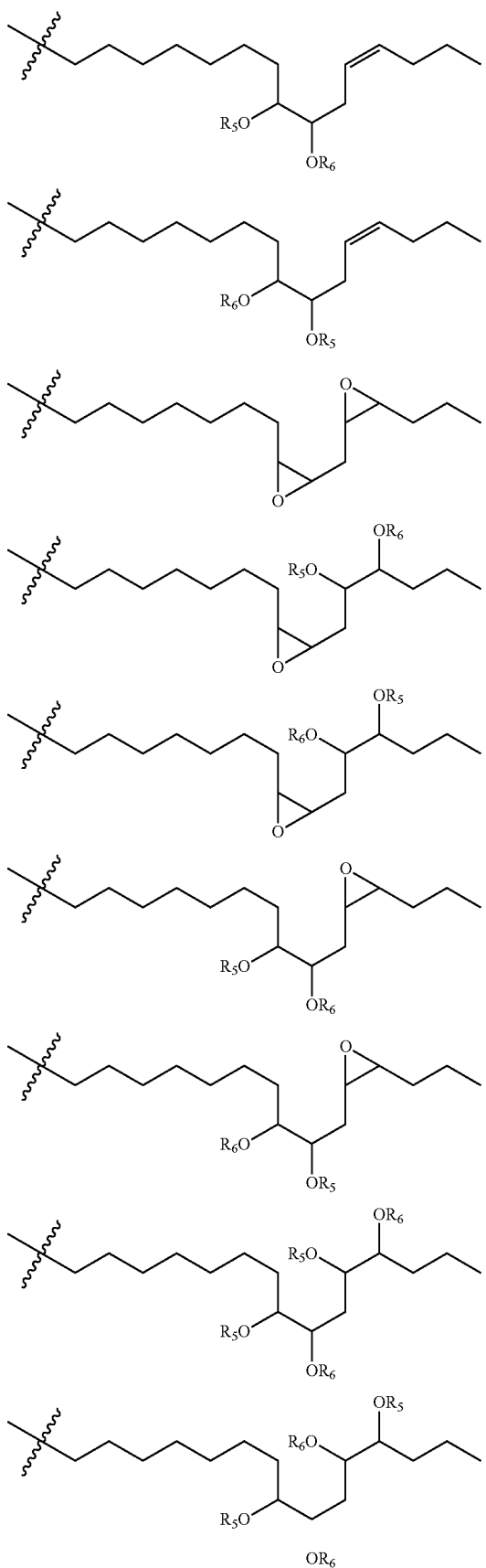
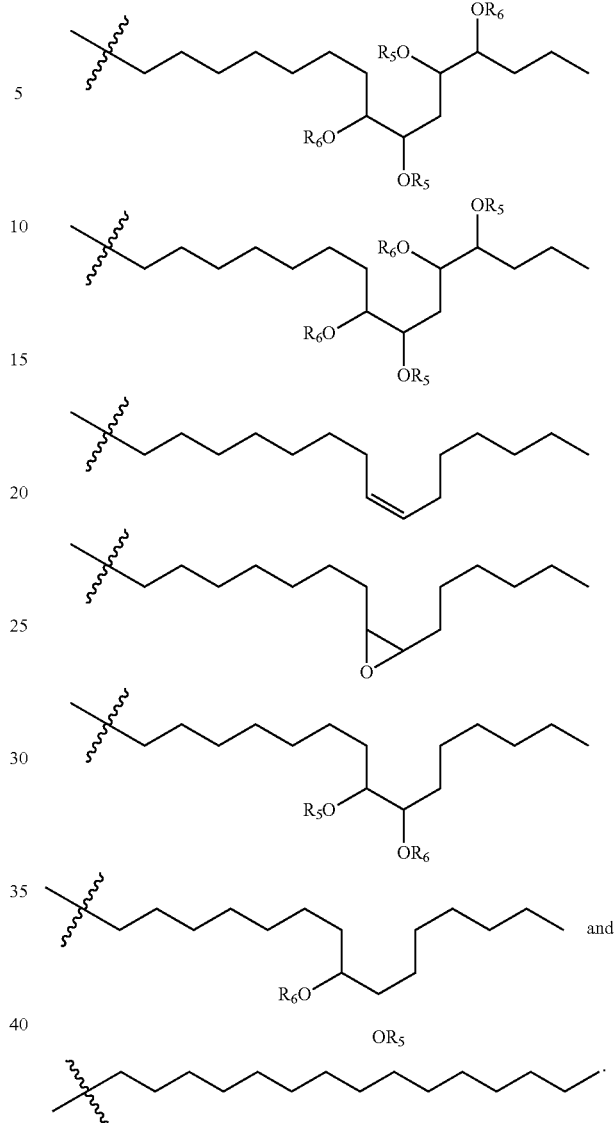

The following step can be achieved in order to reduce resin viscosity. Note that any anhydrides can be used such as acetic anhydride, methacrylic anhydride etc. The following procedure involves the use of acetic anhydride. After distillation of methacrylic acid, heat at 110° C., add 33 mL of acetic anhydride (0.3525 mol, 102.09 g/mol, d=1.08, 5 eq.) and allow to react one hour. Pour ice to cool down the reaction and to neutralize excess of acetic anhydride. After 10 minutes, add slowly 35 mL of cold NaOH 10M and allow to neutralize 5 minutes. Separate the layers and discard the aqueous phase. Add 1.5 L of EtOAc and wash with saturated $NaHCO_3$ until neutral pH. Evaporation of solvent provides acetylated methacrylated cardanol glycidyl diether as a brown viscous resin.

It was thus found, in an example of the present disclosure, that it was possible to prepare compounds, effective to prepare compositions suitable for the preparation of polymers, and that are biobased styrene-free and VOC-free vinylester compounds from vegetable oil with a renewable content that could be increased to 100% with improvement of biobased raw materials chemical transformation technologies. The compositions of the disclosure can comprise compounds (monomers) that come from vegetable oil (cardanol) and a reactive diluent (for example an oleochemical) that can be used in replacement of styrene. In addition of being eco-friendly, safe and obtained from renewable resources, some compounds, derivatives, intermediates and compositions of the present disclosure can be used in order to prepare polymers that have properties and performances of the same order than commercial resins or polymers.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

What is claimed is:

1. A compound of Formula (IVa) or (IVb):

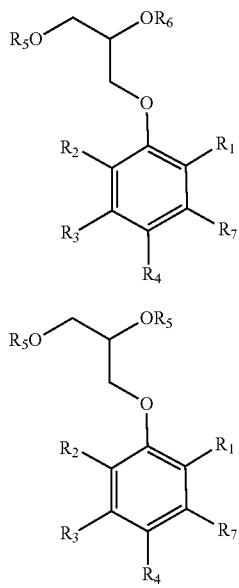

wherein:
$R_1$, $R_2$, $R_3$ and $R_4$ are independently chosen from H, F, Cl, Br, I, OH, O-alkyl, O-aryl, O-acyl and aryl;
$R_5$ is chosen from

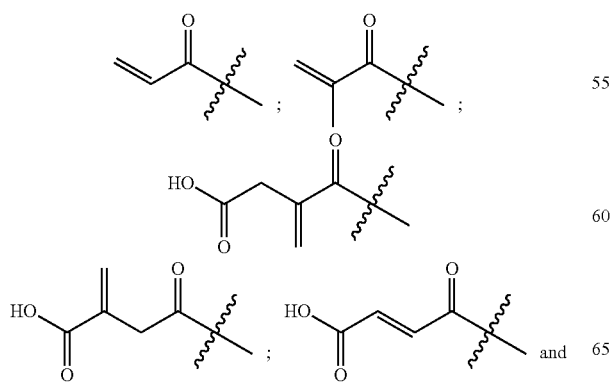

and

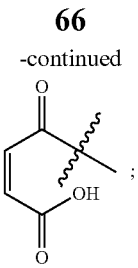

$R_6$ is H or acyl; and
$R_7$ is chosen from

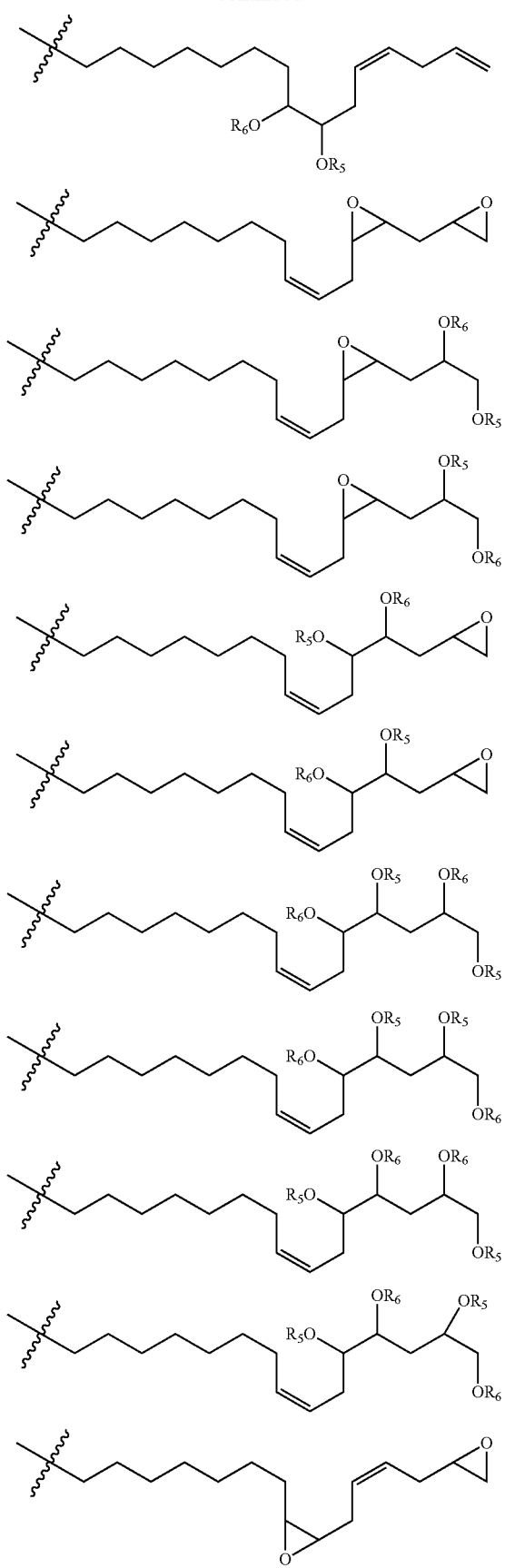
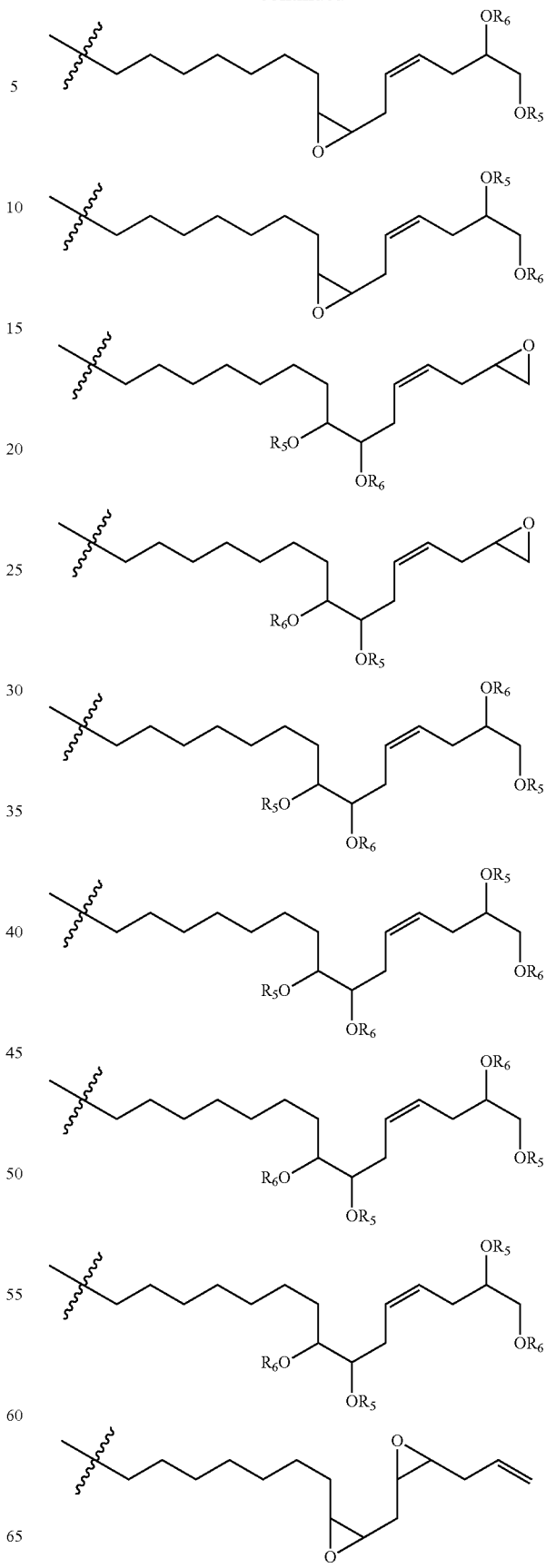

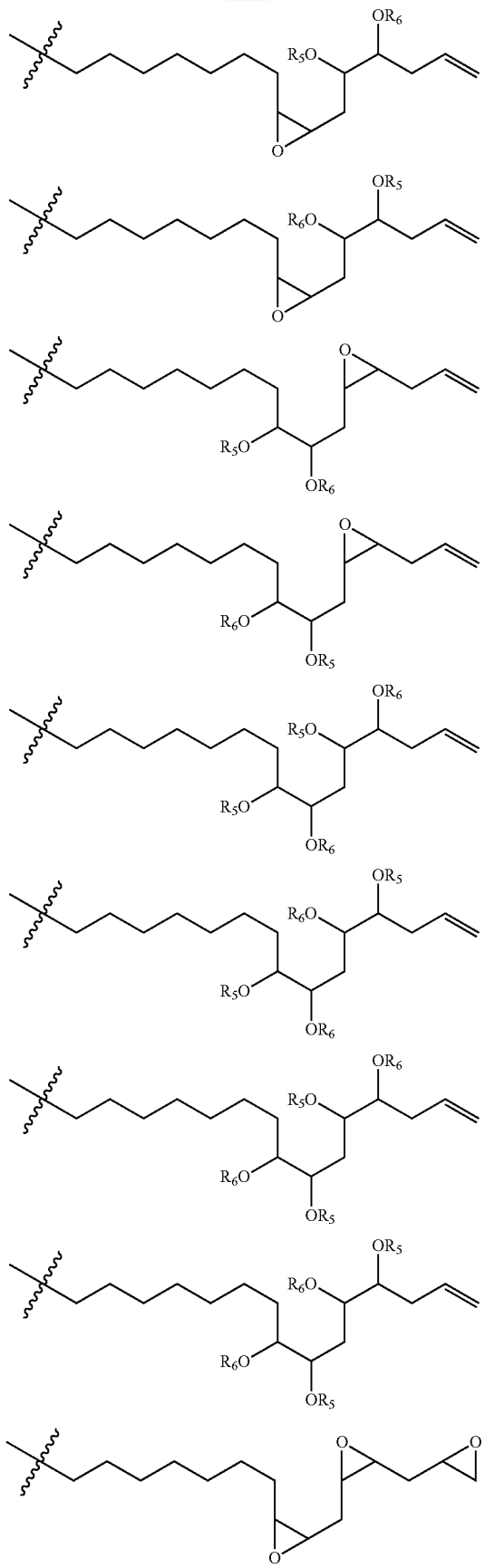
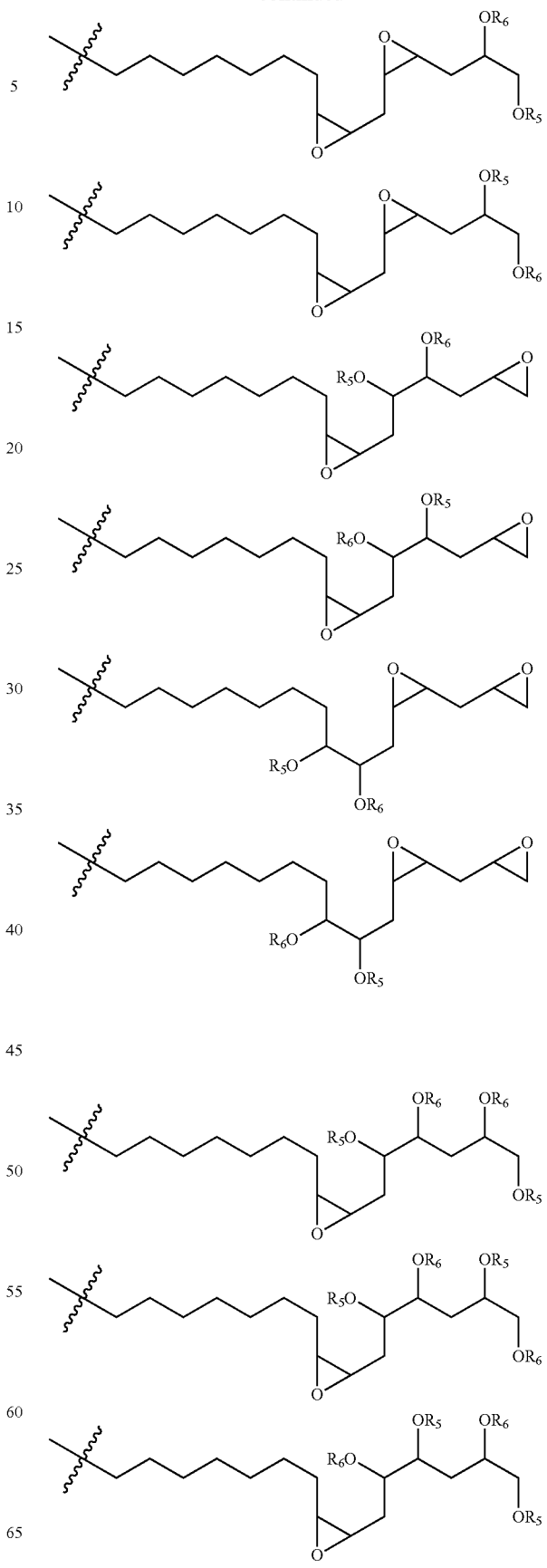

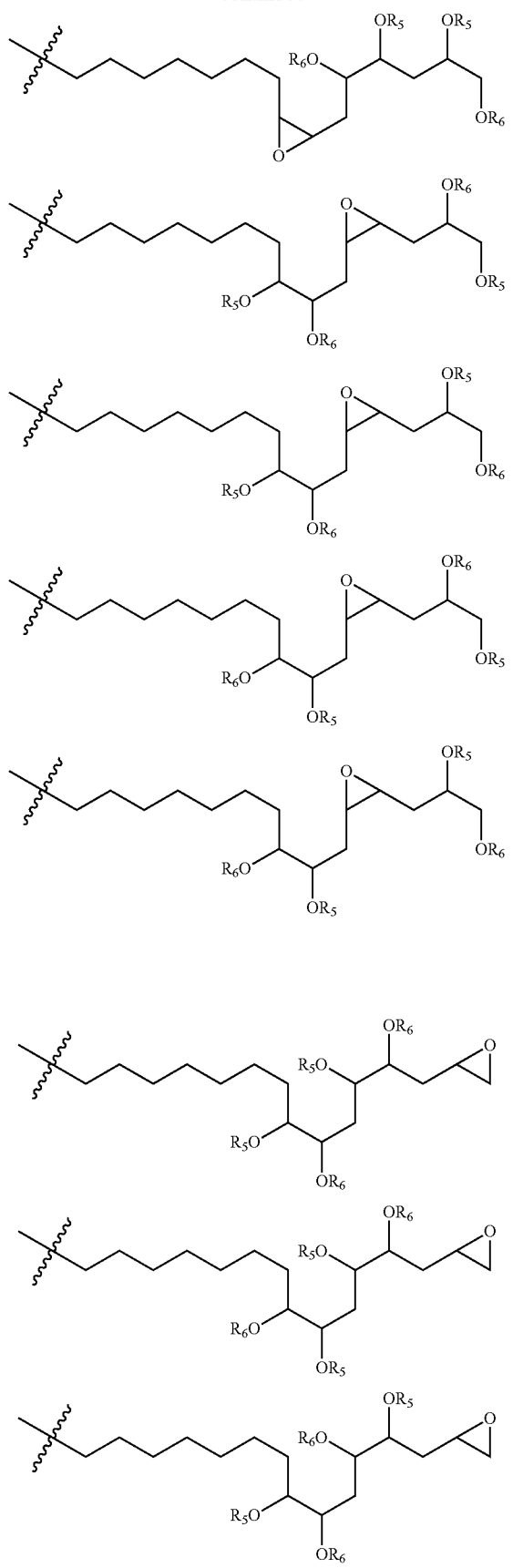
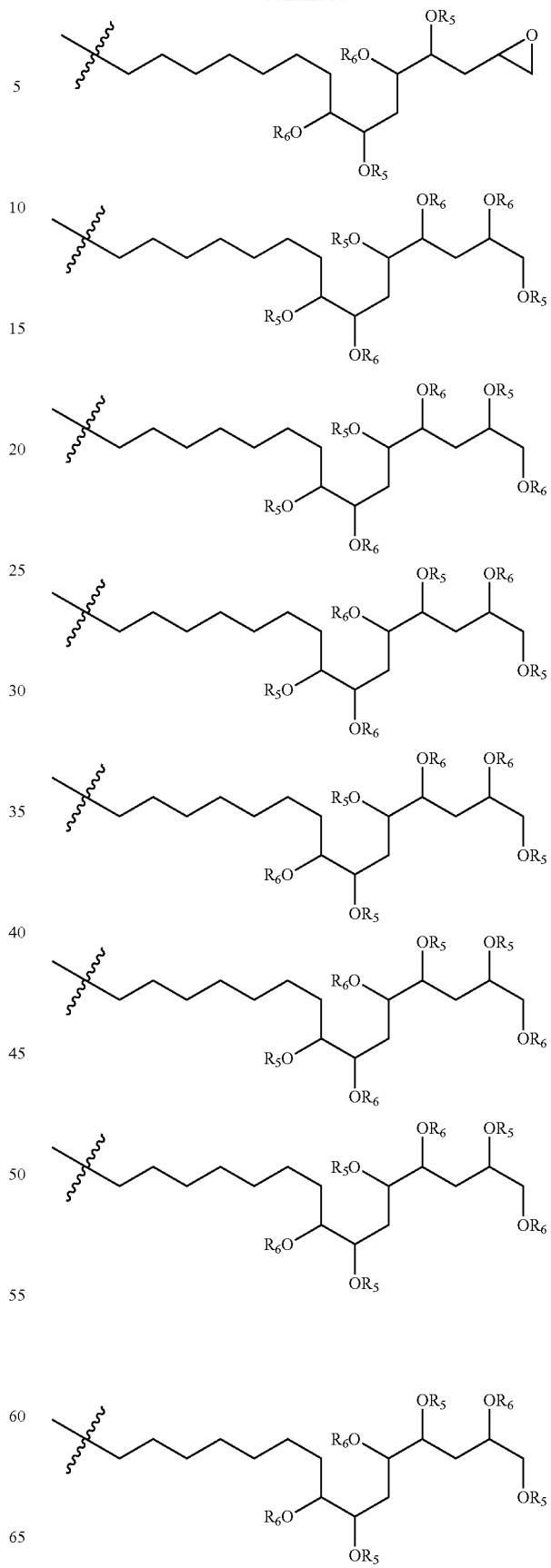

73
-continued
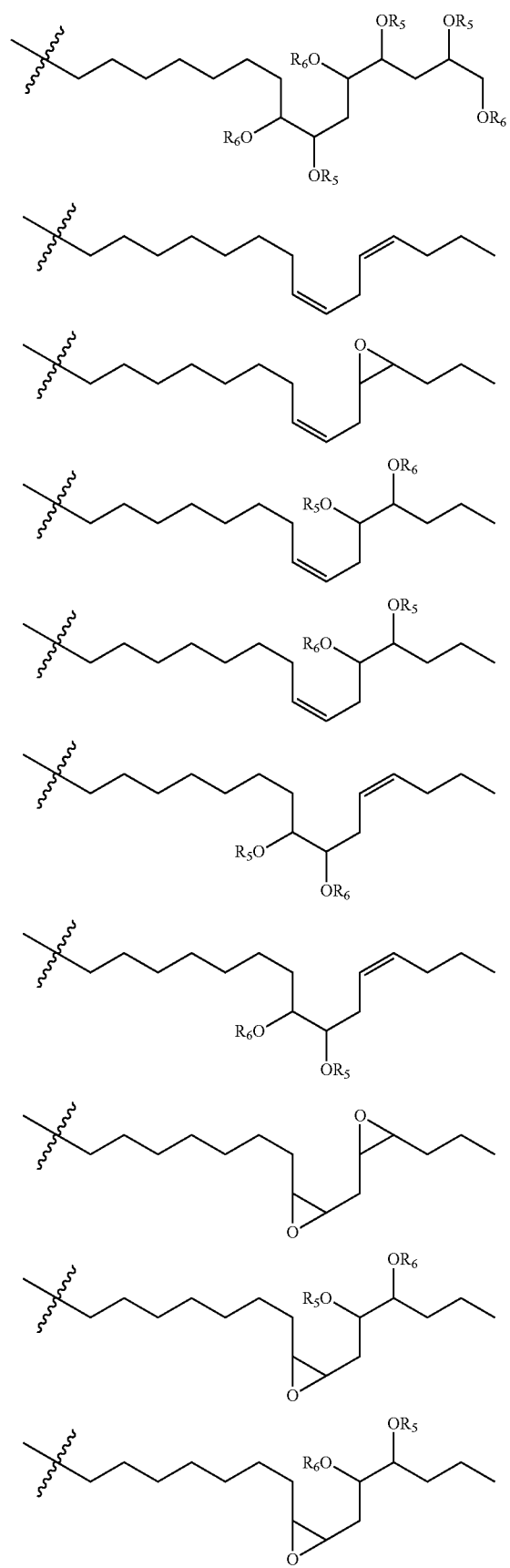
74
-continued
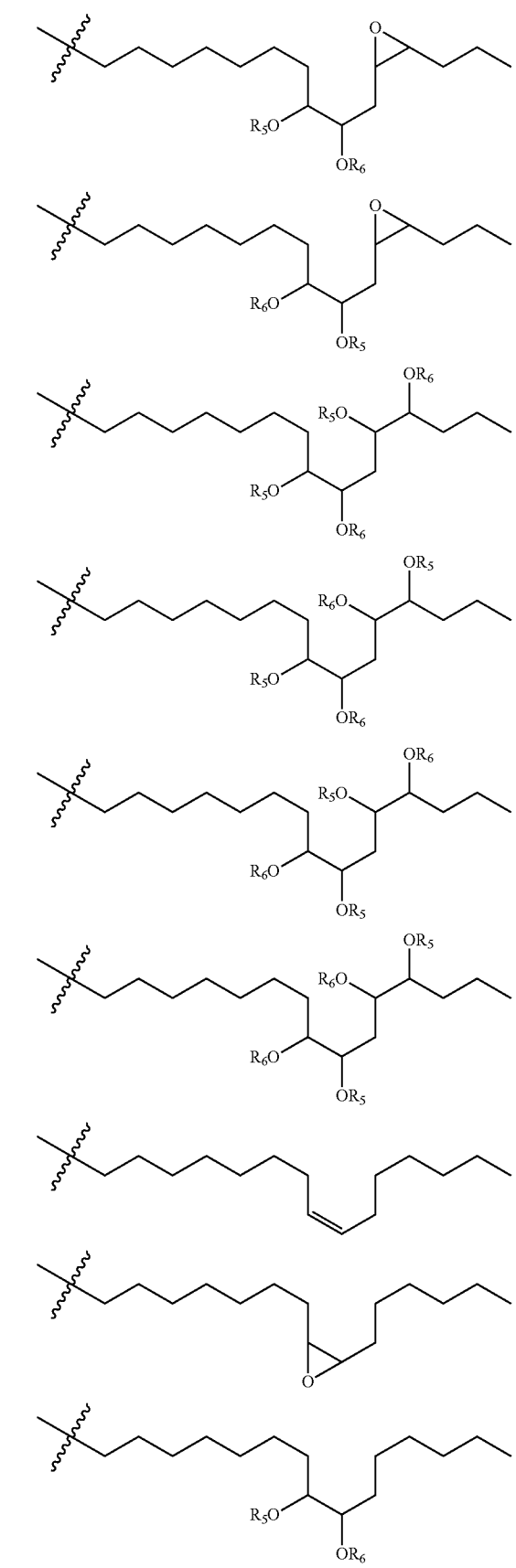

-continued

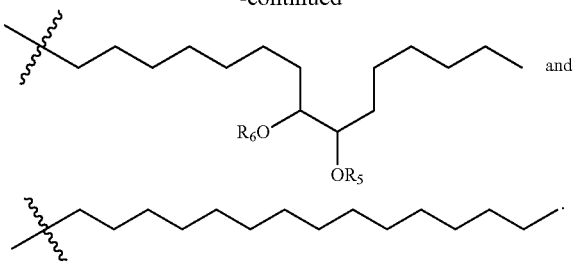
and

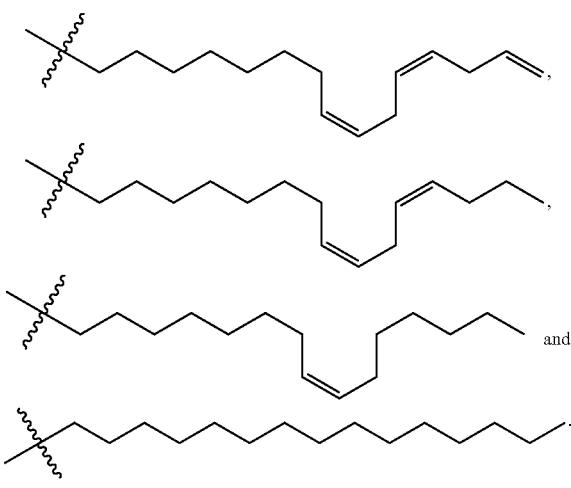

wherein in Formula (IVa) and (IVb), when $R_6$ is H, $R_7$ is different from

2. The compound of claim 1, wherein $R_1$, $R_2$, $R_3$ and $R_4$ are independently chosen from H, F, Cl, Br, I, OH, O-alkyl, O-aryl and O-acyl.

3. The compound of claim 1, wherein $R_1$, $R_2$, $R_3$ and $R_4$ are H.

4. The compound of claim 3, wherein $R_5$ is

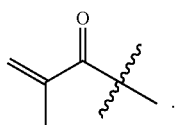 [SMILES: *C(=O)C(=C)C]

5. The compound of claim 4, wherein $R_6$ is H.
6. The compound of claim 4, wherein $R_6$ is acetyl.
7. The compound of claim 1, wherein $R_5$ is

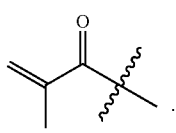 [SMILES: *C(=O)C(=C)C]

8. The compound of claim 1, wherein $R_5$ is

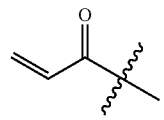

9. The compound of claim 1, wherein $R_5$ is

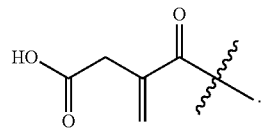

10. The compound of claim 1, wherein $R_5$ is

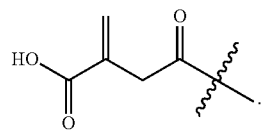

11. The compound of claim 1, wherein $R_5$ is

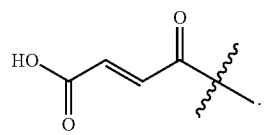

12. The compound of claim 1, wherein $R_5$ is

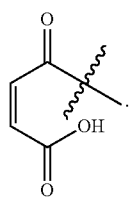

13. The compound of claim 1, wherein $R_6$ is H.
14. The compound of claim 1, wherein $R_6$ is acyl.
15. The compound of claim 1, wherein $R_6$ is acetyl.
16. The compound of claim 13, wherein $R_1$, $R_2$, $R_3$ and $R_4$ are H.
17. The compound of claim 14, wherein $R_1$, $R_2$, $R_3$ and $R_4$ are H.
18. The compound of claim 15, wherein $R_1$, $R_2$, $R_3$ and $R_4$ are H.
19. The compound of claim 16, wherein said compound is a compound of Formula (IVa).
20. The compound of claim 17, wherein said compound is a compound of Formula (IVa).

* * * * *

UNITED STATES PATENT AND TRADEMARK OFFICE
CERTIFICATE OF CORRECTION

PATENT NO. : 10,035,754 B2
APPLICATION NO. : 15/309070
DATED : July 31, 2018
INVENTOR(S) : Thibeault et al.

Page 1 of 1

It is certified that error appears in the above-identified patent and that said Letters Patent is hereby corrected as shown below:

In the Claims

Claim 1, Column 65, Line 35, "R5O" should read -- R6O --

Signed and Sealed this
Twenty-seventh Day of November, 2018

Andrei Iancu
*Director of the United States Patent and Trademark Office*